United States Patent
Kay

(10) Patent No.: US 11,926,861 B2
(45) Date of Patent: Mar. 12, 2024

(54) UTILITIES OF STIMULATED WHOLE BLOOD CULTURE SYSTEMS

(71) Applicant: Heidi Kay, Nashville, TN (US)

(72) Inventor: Heidi Kay, Nashville, TN (US)

(73) Assignee: Heidi Kay, Nashville, TN (US)

( * ) Notice: Subject to any disclaimer, the term of this patent is extended or adjusted under 35 U.S.C. 154(b) by 1 day.

(21) Appl. No.: 16/779,807

(22) Filed: Feb. 3, 2020

(65) Prior Publication Data

US 2021/0002691 A1 Jan. 7, 2021

Related U.S. Application Data

(62) Division of application No. 14/208,086, filed on Mar. 13, 2014, now Pat. No. 10,550,419.

(60) Provisional application No. 61/780,663, filed on Mar. 13, 2013.

(51) Int. Cl.
*C12Q 1/06* (2006.01)
*C12Q 1/02* (2006.01)

(52) U.S. Cl.
CPC ............... *C12Q 1/06* (2013.01); *C12Q 1/025* (2013.01)

(58) Field of Classification Search
None
See application file for complete search history.

(56) References Cited

U.S. PATENT DOCUMENTS

| 5,512,431 A | 4/1996 | Loeb et al. | |
| 5,667,964 A * | 9/1997 | Ho | C12Q 1/703 435/5 |
| 6,410,334 B1 | 6/2002 | Schmolz | |

OTHER PUBLICATIONS

Tang MW, Kanki PJ, Shafer RW. A review of the virological efficacy of the 4 World Health Organization-recommended tenofovir-containing regimens for initial HIV therapy. Clinical infectious diseases : an official publication of the Infectious Diseases Society of America. 2012;54(6):862-75. Epub Feb. 24, 2012.
Tang MW, Liu TF, Shafer RW. The HIVdb system for HIV-1 genotypic resistance interpretation. Intervirology. 2012;55(2):98-101. Epub Jan. 31, 2012.
Tang MW, Shafer RW. HIV-1 antiretroviral resistance: scientific principles and clinical applications. Drugs. 2012;72(9):e1-25. Epub Jun. 13, 2012.
Tasca KI, Calvi SA, Souza Ldo R. Immunovirological parameters and cytokines in HIV infection. Rev Soc Bras Med Trop. Dec. 2012;45(6):663-9.
Teng NN, Lam KS, Calvo Riera F, Kaplan HS. Construction and testing of mouse-human heteromyelomas for human monoclonal antibody production. Proceedings of the National Academy of Sciences of the United States of America. 1983;80(23):7308-12. Epub Dec. 1, 1983.
Thermo Fisher Scientific Plasma and Serum Preparation, 2 pages, 2007, available from www.thermofisher.com/us/en/home/references/protocols/cell-and-tissue-anal- ysis/elisa-protocol/elisa-sample-preparation-protocols/plasma-and- serum-pr- eparation.html#prot4.
Tippett E, Cheng WJ, Westhorpe C, Cameron PU, Brew BJ, Lewin SR, Jaworowski A, Crowe SM. Differential expression of CD163 on monocyte subsets in healthy and HIV-1 infected individuals. PLOS One. 2011;6(5):e19968. doi:10.1371/journal.pone.0019968. Epub May 20, 2011.
Tyagi M, Romerio F. Models of HIV-1 persistence in the CD4+ T cell compartment: past, present and future. Curr HIV Res. 2011;9(8):579-87. Epub Jan. 4, 2012.
Van der Meijden M, Gage J, Breen EC, Taga T, Kishimoto T, Martinez-Maza O. IL-6 receptor (CD126'IL-6R') expression is increased on monocytes and B lymphocytes in HIV infection. Cell Immunol. Dec. 15, 1998;190(2):156-66.
Verhofstede C, Noe A, Demecheleer E, De Cabooter N, Van Wanzeele F, Van Der Gucht B, et al. Drug-resistant variants that evolve during nonsuppressive therapy persist in HIV-1-infected peripheral blood mononuclear cells after long-term highly active antiretroviral therapy. Journal of acquired immune deficiency syndromes. 2004;35(5):473-83. Epub Mar. 17, 2004.
Weber J, Vazquez AC, Winner D, Rose JD, Wylie D, Rhea AM, et al. Novel method for simultaneous quantification of phenotypic resistance to maturation, protease, reverse transcriptase, and integrase HIV inhibitors based on 3'Gag(p2/p7/p1/p6)/PR/RT/INT-recombinant viruses: a useful tool in the multitarget era of antiretroviral therapy. Antimicrobial agents and chemotherapy. 2011;55(8):3729-42. Epub Jun. 2, 2011.
Weinstock HS, Zaidi I, Heneine W, Bennett D, Garcia-Lerma JG, Douglas JM, Jr., et al. The epidemiology of antiretroviral drug resistance among drug-naive HIV-1-infected persons in 10 US cities. J Infect Dis. 2004;189(12):2174-80. Epub Jun. 8, 2004.
Wen W, Chen S, Cao Y, Zhu Y, Yamamoto Y. HIV-1 infection initiates changes in the expression of a wide array of genes in U937 promonocytes and HUT78 T cells. Virus Res. Oct. 2005;113(1):26-35.
Wensing AM, van de Vijver DA, Angarano G, Asjo B, Balotta C, Boeri E, et al. Prevalence of drug-resistant HIV-1 variants in untreated individuals in Europe: implications for clinical management. J Infect Dis. 2005;192(6):958-66. Epub Aug. 19, 2005.
Wheeler WH, Ziebell RA, Zabina H, Pieniazek D, Prejean J, Bodnar UR, et al. Prevalence of transmitted drug resistance associated mutations and HIV-1 subtypes in new HIV-1 diagnoses, U.S.—2006. Aids. 2010;24(8):1203-12. Epub Apr. 17, 2010.

(Continued)

*Primary Examiner* — Stacy B Chen
(74) *Attorney, Agent, or Firm* — Baker, Donelson, Bearman, Caldwell & Berkowitz, P.C.

(57) ABSTRACT

The invention describes a method for determining how to stimulate, monitor and/or inhibit virus production in whole blood culture. The invention relates to a test kit for performing the method and to the use of a suitable blood sampling system. The system can be used to determine how to activate or target latently HIV-infected cells, for clinical management of HIV treatments and for personalized therapeutic strategies.

15 Claims, 6 Drawing Sheets

(56) References Cited

OTHER PUBLICATIONS

WHO HIV drug resistance report 2012. World Health Organization. Geneva, Switzerland. Jul. 2012. ISBN: 978 92 4 150393 8.

WHO Unaids UNICEF Global HIV/AIDS Response: Epidemic update and health sector progress towards Universal Access Progress report. UNICEF, 2011.

King S, Siliciano RF. Targeting HIV latency: pharmacologic strategies toward eradication Drug Discov Today. Author manuscript; available in PMC Jun. 1, 2014. Published in final edited form as: Drug Discov Today. Jun. 2013; 18(0): 541-551. Published online Dec. 25, 2012.

Yukl SA, Boritz E, Busch M, Bentsen C, Chun TW, Douek D, Eisele E, Haase A, Ho YC, Hutter G, Justement JS, Keating S, Lee TH, Li P, Murray D, Palmer S, Pilcher C, Pillai S, Price RW, Rothenberger M, Schacker T, Siliciano J, Siliciano R, Sinclair E, Strain M, Wong J, Richman D, Deeks SG. Challenges in detecting HIV persistence during potentially curative interventions: a study of the Berlin patient. PLOS pathogens. 2013;9(5):e1003347.

Zaccarelli M, Tozzi V, Lorenzini P, Trotta MP, Forbici F, Visco-Comandini U, et al. Multiple drug class-wide resistance associated with poorer survival after treatment failure in a cohort of HIV-infected patients. Aids. 2005;19(10):1081-9. Epub Jun. 17, 2005.

Margolis DM. Mechanisms of HIV latency: an emerging picture of complexity. Curr HIV/AIDS Rep. Feb. 2010;7(1):37-43.

Marini A, Harper JM, Romerio F. An in vitro system to model the establishment and reactivation of HIV-1 latency. J Immunol. Dec. 1, 2008;181(11):7713-20.

Matreyek KA, Oztop I, Freed EO, Engelman A. Viral latency and potential eradication of HIV-1. Expert review of anti-infective therapy. 2012;10(8):855-7. Epub Oct. 4, 2012.

McCloskey TW, Haridas V, Pontrelli L, Pahwa S. Response to superantigen stimulation in peripheral blood mononuclear cells from children perinatally infected with human immunodeficiency virus and receiving highly active antiretroviral therapy. Clin Diagn Lab Immunol. Sep. 2004;11(5):957-62.

McLeod JD, Walker LS, Patel YI, Boulougouris G, Sansom DM. Activation of human T cells with superantigen (staphylococcal enterotoxin B) and CD28 confers resistance to apoptosis via CD95. J Immunol. Mar. 1, 1998;160(5):2072-9.

McNicholas P, Vilchez RA, Greaves W, Kumar S, Onyebuchi C, Black T, et al. Detection of HIV-1 CXCR4 tropism and resistance in treatment experienced subjects receiving CCR5 antagonist-Vicriviroc. Journal of clinical virology : the official publication of the Pan American Society for Clinical Virology. 2012;55(2):134-9.

Menendez-Arias L, Matamoros T, Cases-Gonzalez CE. Insertions and deletions in HIV-1 reverse transcriptase: consequences for drug resistance and viral fitness. Current pharmaceutical design. 2006;12(15):1811-25. Epub May 27, 2006.

Miller DT, Hunsberger BC, Bagwell CB. Automated analysis of GPI-deficient leukocyte flow cytometric data using GemStone.TM . . . Cytometry B Clin Cytom. Sep. 2012;82(5):319-24.

Mohammadi P, Desfarges S, Bartha I, Joos B, Zangger N, Munoz M, Günthard HF, Beerenwinkel N, Telenti A, Ciuffi A. 24 hours in the life of HIV-1 in a T cell line. PLOS Pathog. Jan. 2013;9(1):e1003161.

Moir S, Fauci AS. Pathogenic mechanisms of B-lymphocyte dysfunction in HIV disease. J Allergy Clin Immunol. Jul. 2008;122(1):12-9; quiz 20-1. doi: 10.1016/j.jaci.2008.04.034. Epub Jun. 10, 2008.

Montaner LJ, Crowe SM, Aquaro S, Pero CF, Stevenson M, Collman RG. Advances in macrophage and dendritic cell biology in HIV-1 infection stress keyunderstudied areas in infection, pathogenesis, and analysis of viral reservoirs. J Leukoc Biol. Nov. 2006;80(5):961-4. Epub Aug. 25, 2006.

Montessori, Valentina, et al. "Clinical characteristics of primary HIV infection in injection drug users." AIDS 14.12 (2000): 1868-1870.

Mueller YM, Katsikis PD. IL-15 in HIV infection: pathogenic or therapeutic potential? Eur Cytokine Netw. Sep. 2010;21(3):219-21. doi: 10.1684/ecn.2010.0198. Epub Aug. 19, 2010.

Mugavero MJ, Napravnik S, Cole SR, Eron JJ, Lau B, Crane HM, et al. Viremia copy-years predicts mortality among treatment-naive HIV-infected patients initiating antiretroviral therapy. Clinical infectious diseases : an official publication of the Infectious Diseases Society of America. 2011;53(9):927-35. Epub Sep. 6, 2011.

Murray JM, Kelleher AD, Cooper DA. Timing of the components of the HIV life cycle in productively infected CD4+ T cells in a population of HIV-infected individuals. J Virol. Oct. 2011;85(20):10798-805.

Nalos M, Huang S, Sluyter R, Khan A, Santner-Nanan B, Nanan R, et al. "Host tissue damage" signal ATP impairs IL-12 and IFNgamma secretion in LPS stimulated whole human blood. Intensive Care Med. 2008;34(10):1891-7. Epub Jun. 4, 2008.

North TW, Higgins J, Deere JD, Hayes TL, Villalobos A, Adamson L, et al. Viral sanctuaries during highly active antiretroviral therapy in a nonhuman primate model for Aids. J Virol. 2010;84(6):2913-22. Epub Dec. 25, 2009.

O HIV Persistence and Reactivation: A Proportion of Latent HIV is Missed by Assaying Only Resting CD4 T Cells; Michele Sobolewski; 2017 Conference on Retroviruses and Opportunistic Infections (Feb. 13, 2017-Feb. 16, 2017).

Ogert RA, Wojcik L, Buontempo C, Ba L, Buontempo P, Ralston R, et al. Mapping resistance to the CCR5 co-receptor antagonist vicriviroc using heterologous chimeric HIV-1 envelope genes reveals key determinants in the C2-V5 domain of gp120. Virology. 2008;373(2):387-99. Epub Jan. 15, 2008.

Panel on Antiretroviral Guidelines for Adults and Adolescents. Guidelines for the use of antiretroviral agents in HIV-1-infected adults and adolescents. Department of Health and Human Services. Available at http://aidsinfo.nih.gov/ContentFiles/AdultandAdolescentGL.pdf. aidsinfo, 2013.

Parisi SG, Boldrin C, Cruciani M, Nicolini G, Cerbaro I, Manfrin V, et al. Both human immunodeficiency virus cellular DNA sequencing and plasma RNA sequencing are useful for detection of drug resistance mutations in blood samples from antiretroviral-drug-naive patients. J Clin Microbiol. Jun. 2007;45(6):1783-8. Epub Apr. 18, 2007.

Paterson DL, Swindells S, Mohr J, Brester M, Vergis EN, Squier C, et al. Adherence to protease inhibitor therapy and outcomes in patients with HIV infection. Ann Intern Med. 2000;133(1):21-30. Epub Jul. 6, 2000.

Patterson BK, McCallister S, Schutz M, Siegel JN, Shults K, Flener Z, et al. Persistence of intracellular HIV-1 mRNA correlates with HIV-1-specific immune responses in infected subjects on stable HAART. Aids. 2001;15(13):1635-41. Epub Sep. 8, 2001.

Perelson AS, Neumann AU, Markowitz M, Leonard JM, Ho DD. HIV-1 dynamics in vivo: virion clearance rate, infected cell lifespan, and viral generation time. Science. 1996;271(5255):1582-6. Epub Mar. 15, 1996.

Planelles V, Wolschendorf F, Kutsch O. Facts and fiction: cellular models for high throughput screening for HIV-1 reactivating drugs. Curr HIV Res. Dec. 1, 2011;9(8):568-78.

Procopio FA, Fromentin R, Kulpa DA, Brehm JH, Bebin AG, Strain MC, Richman DD, O'Doherty U, Palmer S, Hecht FM, Hoh R, Barnard RJ, Miller MD, Hazuda DJ, Deeks SG, Sekaly RP, Chomont N. A Novel Assay to Measure the Magnitude of the Inducible Viral Reservoir in HIV-infected Individuals. EBioMedicine. Jun. 27, 2015;2(8):874-83.

Chun TW. Tracking replication-competent HIV reservoirs in infected individuals. Curr Opin HIV AIDS. Mar. 2013;8(2):111-6.

Coiras M, Lopez-Huertas MR, Perez-Olmeda M, Alcami J. Understanding HIV-1 latency provides clues for the eradication of long-term reservoirs. Nat Rev Microbiol. 2009;7(11):798-812. Epub Oct. 17, 2009.

Colin L, Van Lint C. Molecular control of HIV-1 postintegration latency: implications for the development of new therapeutic strategies. Retrovirology. 2009;6:111. Epub Dec. 8, 2009.

Conti P, Barbacane RC, Feliciani C, Reale M. Expression and secretion of RANTES by human peripheral blood CD4+ cells are dependent on the presence of monocytes. Ann Clin Lab Sci. Jan. 2001;31(1):75-84.

Cortez KJ, Maldarelli F. Clinical management of HIV drug resistance. Viruses. 2011;3(4):347-78. Epub Oct. 14, 2011.

Cozzi-Lepri A, Phillips AN, Clotet B, Mocroft A, Ruiz L, Kirk O, et al. Detection of HIV drug resistance during antiretroviral treat-

(56) References Cited

OTHER PUBLICATIONS ment and clinical progression in a large European cohort study. Aids. 2008;22(16):2187-98. Epub Oct. 4, 2008.
Crum NF, Riffenburgh RH, Wegner S, Agan BK, Tasker SA, Spooner KM, et al. Comparisons of causes of death and mortality rates among HIV-infected persons: analysis of the pre-, early, and late HAART (highly active antiretroviral therapy) eras. Journal of acquired immune deficiency syndromes. 2006;41(2):194-200. Epub Jan. 6, 2006.
Dalmau J, Codoner FM, Erkizia I, Pino M, Pou C, Paredes R, et al. In-depth characterization of viral isolates from plasma and cells compared with plasma circulating quasispecies in early HIV-1 infection. PloS one. 2012;7(2):e32714. Epub Mar. 7, 2012.
Davey RT, Jr., Bhat N, Yoder C, Chun TW, Metcalf JA, Dewar R, et al. HIV-1 and T cell dynamics after interruption of highly active antiretroviral therapy (HAART) in patients with a history of sustained viral suppression. Proceedings of the National Academy of Sciences of the United States of America. 1999,96(26):15109-14. Epub Dec. 28, 1999.
De Boer RJ, Ribeiro RM, Perelson AS. Current estimates for HIV-1 production imply rapid viral clearance in lymphoid issues. PLoS computational biology. 2010;6(9):e1000906. Epub Sep. 9, 2010.
Deeks SG, Gange SJ, Kitahata MM, Saag MS, Justice AC, Hogg RS, et al. Trends in multidrug treatment failure and subsequent mortality among antiretroviral therapy-experienced patients with HIV infection in North America. Clinical Infectious diseases : an official publication of the Infectious Diseases Society of America. 2009;49(10):1582-90. Epub Oct. 23, 2009.
Deeks SG. HIV: Shock and kill. Nature. 2012;487(7408):439-40. Epub Jul. 28, 2012.
Deere JD, Schinazi RF, North TW. Simian immunodeficiency virus macaque models of HIV latency. Curr Opin HIV AIDS. 2011;6(1):57-61. Epub Jan. 19, 2011.
Douek DC, Brenchley JM, Betts MR, Ambrozak DR, Hill BJ, Okamoto Y, Casazza JP, Kuruppu J, Kunstman K, Wolinsky S, Grossman Z, Dybul M, Oxenius A, Price DA, Connors M, Koup RA. HIV preferentially infects HIV-specific CD4+ T cells. Nature. May 2, 2002;417(6884):95-8.
Duffy D, Rouilly V, Libri V, Hasan M, Beitz B, David M, Urrutia A, Bisiaux A, Labrie ST, Dubois A, Boneca IG, Delval C, Thomas S, Rogge L, Schmalz M, Quintana-Murci L, Albert ML; Milieu Interieur Consortium. Functional analysis via standardized whole-blood stimulation systems defines the boundaries of a healthy immune response to complex stimuli. Immunity. Mar. 20, 2014;40(3):436-50.
Dunne AL, Mitchell FM, Coberly SK, Hellmann NS, Hoy J, Mijch A, et al. Comparison of genotyping and phenotyping methods for determining susceptibility of HIV-1 to antiretroviral drugs. Aids. 2001;15(12):1471-5. Epub Aug. 16, 2001.
Duverger A, Wolschendorf F, Zhang M, Wagner F, Hatcher B, Jones J, Cron RQ, van der Sluis RM, Jeeninga RE, Berkhout B, Kutsch O. An AP-1 binding site in the enhancer/core element of the HIV-1 promoter controls the ability of HIV-1 to establish latent infection. J Virol. Feb. 2013;87(4):2264-77.
Duyne RV, Narayanan A, K KH, Saifuddin M, Shultz L, Kashanchi F. Humanized mouse models of HIV-1 latency. Curr HIV Res. 2011;9(8):595-605. Epub Jan. 4, 2012.
Dybul M, Fauci AS, Bartlett JG, Kaplan JE, Pau AK. Guidelines for using antiretroviral agents among HIV-infected adults and adolescents. Recommendations of the Panel on Clinical Practices for Treatment of HIV. Panel on Clinical Practices for the Treatment of HIV.MMWR Recomm Rep. May 17, 2002; 51(RR-7):1-55.
Eisele E, Siliciano RF. Redefining the viral reservoirs that prevent HIV-1 eradication. Immunity. Sep. 21, 2012;37(3):377-88.
Eriksson S, Graf EH, Dahl V, et al. Comparative Analysis of Measures of Viral Reservoirs in HIV-1 Eradication Studies. Douek DC, ed. PLoS Pathogens. 2013;9(2):e1003174.
Eugenin EA, Osiecki K, Lopez L, Goldstein H, Calderon TM, Berman JW. CCL2/monocyte chemoattractant protein-1 mediates enhanced transmigration of human immunodeficiency virus (HIV)-infected leukocytes across the blood-brain barrier: a potential mechanism of HIV-CNS invasion and NeuroAIDS. J Neurosci. Jan. 25, 2006;26(4):1098-106.
Farnham PG. Do reduced inpatient costs associated with highly active antiretroviral therapy (HAART) balance the overall cost for HIV treatment? Applied health economics and health policy. 2010;8(2):75-88. Epub Feb. 24, 2010.
Fritsch RD, Shen X, Sims GP, Hathcock KS, Hodes RJ, Lipsky PE. Stepwise differentiation of CD4 memory T cells defined by expression of CCR7 and CD27. J Immunol. 2005; 175(10):6489-97. Epub Nov. 8, 2005.
Gandhi T, Nagappan V, Cinti S, Wei W, Kazanjian P. Long-term immunologic and virologic responses in patients with highly resistant HIV infection who are treated with an incompletely suppressive antiretroviral regimen. Clinical infectious diseases : an official publication of the Infectious Diseases Society of America. 2007;45(8):1085-92. Epub Sep. 21, 2007.
Geretti AM. Epidemiology of antiretroviral drug resistance in drug-naive persons. Curr Opin Infect Dis. 2007;20(1):22-32. Epub Jan. 2, 2007.
Abbott RealTime HIV-1 package insert instructions, Dec. 2011, 11 pages, available from www.abbottmolecular.com/en-us/staticAssets/pdfs/US/realtime-hiv-1-package--insert.pdf.
ACH-2 Cells Data Sheet, NIH AIDS Reagent Program, Rev: Oct. 22, 2018.
Alexaki A, Liu Y, Wigdahl B. Cellular reservoirs of HIV-1 and their role in viral persistence. Curr HIV Res. Sep. 2008;6(5):388-400.
Anton PA, Mitsuyasu RT, Deeks SG, Scadden DT, Wagner B, Huang C, Macken C, Richman DD, Christopherson C, Borellini F, Lazar R, Hege KM. Multiple measures of HIV burden in blood and tissue are correlated with each other but hot with clinical parameters in aviremic subjects. AIDS. Jan. 3, 2003;17(1):53-63.
Archin N, Liberty A, Kashuba A, et al. Administration of vorinostat disrupts HIV-1 latency in patients on antiretroviral therapy. Nature. 2012;487(7408):482-485.
Archin NM, Bateson R, Tripathy MK, Crooks AM, Yang KH, Dahl NP, Kearney MF, Anderson EM, Coffin JM, Strain MC, Richman DD, Robertson KR, Kashuba AD, Bosch RJ, Hazuda DJ, Kuruc JD, Eron JJ, Margolis DM. HIV-1 expression within resting CD4+ T cells after multiple doses of vorinostat. J Infect Dis. Sep. 1, 2014;210(5):728-35.
Archin NM, Cheema M, Parker D, Wiegand A, Bosch RJ, Coffin JM, Eron J, Cohen M, Margolis DM. Antiretroviral Intensification and Valproic Acid Lack Sustained Effect on Residual HIV-1 Viremia or Resting CD4+ Cell Infection. PLoS ONE. 2010;5(2):e9390.
Ariza ME, Ramakrishnan R, Singh NP, Chauhan A, Nagarkatti PS, Nagarkatti M. Bryostatin-1, a naturally occurring antineoplastic agent, acts as a Toll-like receptor 4 (TLR-4) ligand and induces unique cytokines and chemokines in dendritic cells. J Biol Chem. Jan. 7, 2011;286(1):24-34.
Bannister WP, Cozzi-Lepri A, Kjaer J, Clotet B, Lazzarin A, Viard JP, et al. Estimating prevalence of accumulated HIV-1 drug resistance in a cohort of patients on antiretroviral therapy. The Journal of antimicrobial chemotherapy. 2011;66(4):901-11. Epub Mar. 12, 2011.
Barker E, Bossart KN, Levy JA. Differential effects of CD28 costimulation on HIV production by CD4+ cells. J Immunol. Dec. 1, 1998;161(11):6223-7.
Barnett PG, Chow A, Joyce VR, Bayoumi AM, Griffin SC, Nosyk B, et al. Determinants of the cost of health services used by veterans with HIV. Medical care. 2011;49(9):848-56. Epub May 26, 2011.
Battistini A, Sgarbanti M. HIV-1 latency: an update of molecular mechanisms and therapeutic strategies. Viruses. 2014;8(4):1715-58.
Benyoucef et al (Journal of Virological Methods 71:123-131, 1998).
Bocklandt et al., Antiviral Research, 2003, 59(2):89-98. (Year: 2003).
Bosque A, Planelles V. Induction of HIV-1 latency and reactivation in primary memory CD4+ T cells. Blood. Jan. 1, 2009;113(1):58-65.
Brooks DG, Arlen PA, Gao L, Kitchen CM, Zack JA. Identification of Tcell-signaling pathways that stimulate latent HIV in primary cells. Proc Natl Acad Sci U S A. Oct. 28, 2003; 100(22):12955-60. Epub Oct. 20, 2003.

(56) References Cited

OTHER PUBLICATIONS

Brumme ZL, John M, Carlson JM, Brumme CJ, Chan D, Brockman MA, Swenson LC, Tao I, Szeto S, Rosato P, Sela J, Kadie CM, Frahm N, Brander C, Haas DW, Riddler SA, Haubrich R, Walker BD, Harrigan PR, Heckerman D, Mallal S. HLA-associated immune escape pathways in HIV-1 subtype B Gag, Pol and Nef proteins. PLoS One. Aug. 19, 2009;4(8):e6687.

Cane P, Chrystie I, Dunn D, Evans B, Geretti AM, Green H, et al. Time trends in primary resistance to HIV drugs in the United Kingdom: multicentre observational study. BMJ. 2005;331(7529):1368. Epub Nov. 22, 2005.

Cassol E, Alfano M, Biswas P, Poli G. Monocyte-derived macrophages and myeloid cell lines as targets of HIV-1 replication and persistence. J Leukoc Biol. Nov. 2006;80(5):1018-30. Epub Aug. 31, 2006.

Chan CN, Dietrich I, Hosie MJ, Willett BJ. Recent developments in human immunodeficiency virus-1 latency research. The Journal of general virology. 2013;94(Pt 5):917-32. Epub Feb. 1, 2013.

Chaponda M, Pirmohamed M. Hypersensitivity reactions to HIV therapy. Br J Clin Pharmacol. May 2011;71(5):659-71.

Chesney, MA. The elusive gold standard. Future perspectives for HIV adherence assessment and intervention. J Acquir Immune Defic Syndr. 2006;43 Suppl 1:S149-155.

Chiu YL, Soros VB, Kreisberg JF, Stopak K, Yonemoto W, Greene WC. Cellular APOBEC3G restricts HIV-1 infection In resting CD4+ T cells. Nature. 2005;435(7038):108-14. Epub Apr. 15, 2005.

Chopera DR, Wright JK, Brockman MA, Brumme ZL. Immune-mediated attenuation of HIV-1. Future Virol. Aug. 2011;6(8):917-928.

Chun TW, Fauci AS. HIV reservoirs: pathogenesis and obstacles to viral eradication and cure. AIDS. Jun. 19, 2012;26(10):1261-8.

Chun TW, Justement JS, Murray D, Hallahan CW, Maenza J, Collier AC, et al. Rebound of plasma viremia following cessation of antiretroviral therapy despite profoundly low levels of HIV reservoir: implications for eradication. Aids. 2010;24(18):2803-8. Epub Oct. 22, 2010.

Chun TW, Stuyver L, Mizell SB, Ehler LA, Mican JA, Baseler M, Lloyd AL, Nowak MA, Fauci AS. Presence of an inducible HIV-1 latent reservoir during highlyactive antiretroviral therapy. Proc Natl Acad Sci U S A. Nov. 25, 1997;94(24):13193-7.

Rasmussen TA, Tolstrup M, Brinkmann CR, Olesen R, Erikstrup C, Solomon A, Winckelmann A, Palmer S, Dinarello C, Buzon M, Lichterfeld M, Lewin SR, Østergaard L, Søgaard OS. Panobinostat, a histone deacetylase inhibitor, for latent-virus reactivation in HIV-infected patients on suppressive antiretroviral therapy: a phase 1/2, single group, clinical trial. Lancet HIV. Oct. 2014;1(1):e13-21.

Recordon-Pinson P, Soulie C, Flandre P, Descamps D, Lazrek M, Charpentier C, et al. Evaluation of the genotypic prediction of HIV-1 coreceptor use versus a phenotypic assay and correlation with the virological response to maraviroc: the ANRS GenoTropism study. Antimicrobial agents and chemotherapy. 2010;54(8):3335-40. Epub Jun. 10, 2010.

Riley JL, Levine BL, Craighead N, Francomano T, Kim D, Carroll RG, June CH. Naïve and memory CD4 T cells differ in their susceptibilities to human immunodeficiency virus type 1 infection following CD28 costimulation: implicatip6s for transmission and pathogenesis. J Virol. Oct. 1998;72(10):8273-80.

Roederer M, Raju PA, Mitra DK, Herzenberg LA, Herzenberg LA. HIV does not replicate in naive CD4 T cells stimulated with CD3/CD28. J Clin Invest. Apr. 1, 1997;99(7):1555-64.

Romani B, Engelbrecht S, Glashoff RH. Antiviral roles of APOBEC proteins against HIV-1 and suppression by Vif. Arch Virol. 2009;154(10):1579-88. Epub Aug. 12, 2009.

Sahu GK, Lee K, Ji J, Braciale V, Baron S, Cloyd MW. A novel in vitro system to generate and study latently HIV-infected long-lived normal CD4+ T-lymphocytes. Virology. Nov. 25, 2006;355(2):127-37. Epub Aug. 17, 2006.

Saleh S, Wightman F, Ramanayake S, Alexander M, Kumar N, Khoury G, Pereira C, Purcell D, Cameron PU, Lewin SR. Expression and reactivation of HIV in a chemokine induced model of HIV latency in primary resting CD4+ T cells. Retrovirology. Oct. 12, 2011;8:80.

Savarino A, Bottarel F, Malavasi F, Dianzani U. Role of CD38 in HIV-1 infection: an epiphenomenon of T-cell activation or an active player in virus/host interactions? AIDS. Jun. 16, 2000;14(9):1079-89.

Schmolz M, Hurst TL, Bailey DM, Powell JR, Forsey RJ, Thompson JM, et al. Validation of a new highly standardised, lab-independent whole-blood leukocyte function assay for clinical trials (ILCS). Exp Gerontol. 2004;39(4):667-71. Epub Mar. 31, 2004.

Schmolz M, Hurst TL, Bailey DM, Powell JR, Forsey RJ, Thompson JM, et al. Validation of a new highly standardised, ab-independent whole-blood leukocyte function assay for clinical trials (ILCS). Experimental gerontology. 2004;39 (4):667-71. Epub Mar. 31, 2004.

Schroder K, Tschopp J. The inflammasomes. Cell. Mar. 19, 2010;140(6):821-32.

Schüpbach J. Viral RNA and p24 antigen as markers of HIV disease and antiretroviral treatment success. Int Arch Allergy Immunol. Nov. 2003;132(3):196-209.

Secchiero P, Zella D, Curreli S, Mirandola P, Capitani S, Gallo RC, Zauli G.Engagement of CD28 modulates CXC chemokine receptor 4 surface expression in both resting and CD3-stimulated CD4+ T cells. J Immunol. Apr. 15, 2000;164(8):4018-24.

Shan L, Deng K, Shroff NS, Durand CM, Rabi SA, Yang HC, Zhang H, Margolick JB, Blankson JN, Siliciano RF. Stimulation of HIV-1-specific cytolytic T-lymphocytes facilitates elimination of latent viral reservoir after virus reactivation. Immunity. 2012;36(3):491-501.

Shete A, Thakar M, Singh DP, Gangakhedkar R, Gaikwad A, Pawar J, et al. Short communication: HIV antigen-specific reactivation of HIV infection from cellular reservoirs: implications in the settings of therapeutic vaccinations. AIDS research and human retroviruses. 2012;28(8):835-43. Epub Sep. 23, 2011.

Biliciano RF, Greene WC. HIV latency. Cold Spring Harb Perspect Med. Sep. 2011;1(1):a007096.

Siliciano RF. HIV-1 Eradication Strategies: Design and Assessment. Curr Opin HIV AIDS. Jul. 2013: 8(4) 318-325.

Smith MZ, Wightman F, Lewin SR. HIV reservoirs and strategies for eradication. Curr HIV/AIDS Rep. 2012;9(1):5-15. Epub Jan. 18, 2012.

Smith MZ, Wightman F, Lewin SR. HIV reservoirs and strategies for eradication. Current HIV/AIDS reports. 2012;9(1):5-15. Epub Jan. 18, 2012.

Sousa AE, Carneiro J, Meier-Schellersheim M, Grossman Z, Victorino RM. CD4 I cell depletion is linked directly to immune activation in the pathogenesis of HIV-1 and HIV-2 but only indirectly to the viral load. J Immunol. Sep. 15, 2002;169(6):3400-6.

Spina CA, Anderson J, Archin NM, Bosque A, Chan J, Famiglielli M, Greene WC, Kashuba A, Lewin SR, Margolis DM, Mau M, Ruelas D, Saleh S, Shirakawa K, Siliciano RF, Singhania A, Soto PC, Terry VH, Verdin E, Woelk C, Wooden S, Xing S, Planelles V. An In-Depth Comparison of Latent HIV-1 Reactivation in Multiple Cell Model Systems and Resting CD4+ T Cells from Aviremic Patients. PLoS Pathog. 2013; 9(12): e1003834.

Spina, Celsa A., et al. "An in-depth comparison of latent HIV-1 reactivation in multiple cell model systems and resting CD4+ T cells from aviremic patients." PLoS pathogens 9.12 (2013): e1003834.

Spivak AM, Andrade A, Eisele E, Hoh R, Bacchetti P, Bumpus NN, Emad F, Buckheit R 3rd, McCance-Katz EF, Lai J, Kennedy M, Chander G, Siliciano RF, Siliciano JD, Deeks SG. A pilot study assessing the safety and latency-reversing activity of disulfiram in HIV-1-infected adults on antiretroviral therapy. Clin Infect Dis. Mar. 2014,58(6):883-90.

Stedman, Thomas Lathrop. "Stedman's Medical Dictionation" (27th edition, 2000).

Strickland SL, Gray RR, Lamers SL, Burdo TH, Huenink E, Nolan DJ, et al. Efficient transmission and persistence of low-frequency SIVmac251 variants in CD8-depleted rhesus macaques with different neuropathology. J Gen Virol. 2012;93(Pt 5):925-38. Epub Feb. 4, 2012.

(56) References Cited

OTHER PUBLICATIONS

Sunshine, Sara, et al. "HIV integration site analysis of cellular models of HIV latency with a probe-enriched next-generation sequencing assay." Journal of virology 90.9 (2016): 4511-4519.
Grover D, Copas A, Green H, Edwards SG, Dunn DT, Sabin C, et al. What is the risk of mortality following diagnosis of multidrug-resistant HIV-1? The Journal of antimicrobial chemotherapy. 2008;61(3):705-13. Epub Jan. 29, 2008.
Haggerty CM, Pitt E, Siliciano RF. The latent reservoir for HIV-1 in resting CD4+ T cells and other viral reservoirs during chronic infection: insights from treatment and treatment-interruption trials. Curr Opin HIV AIDS. 2006; 1(1):62-8. Epub Jan. 1, 2006.
Hatano H, Jain V, Hunt PW, Lee TH, Sinclair E, Do TD, Hoh R, Martin JN, McCune JM, Hecht F, Busch MP, Deeks SG. Cell-based measures of viral persistence are associated with immune activation and programmed cell death protein 1 (PD-1)-expressing CD4+ T cells. J Infect Dis. Jul. 2013;208(1):50-6. epub Oct. 22, 2012.
Henrich TJ, Gallien S, Li JZ, Pereyra F, Kuritzkes DR. Low-level detection and quantitation of cellular HIV-1 DNA and 2-LTR circles using droplet digital Pcr. J Virol Methods. Dec. 2012;186(1-2):68-72. doi: 10.1016/j.viromet.2012.08.019. Epub Sep. 4, 2012.
Hertogs K, de Bethune MP, Miller V, Ivens T, Schel P, Van Cauwenberge A, et al. A rapid method for simultaneous detection of phenotypic resistance to inhibitors of protease and reverse transcriptase in recombinant human immunodeficiency virus type 1 isolates from patients treated with antiretroviral drugs. Antimicrobial agents and chemotherapy. 1998;42(2):269-76. Epub Apr. 4, 1998.
HIV in the United States: At a Glance, National Center for HIV/AIDS, Viral Hepatitis, STD and TB Prevention, Division of HIV/AIDS Prevention. 2013.
Ho YC, Shan L, Hosmane NN, Wang J, Laskey SB, Rosenbloom DI, Lai J, Blankson JN, Siliciano JD, Siliciano RF. Replication-competent noninduced proviruses in the latent reservoir increase barrier to HIV-1 cure. Cell. Oct. 24, 2013;155(3):540-51.
Jaafoura S, de Goër de Herve MG, Hernandez-Vargas EA, Hendel-Chavez H, Abdoh M, Mateo MC, Krzysiek R, Merad M, Seng R, Tardieu M, Delfraissy JF, Goujard C, Taoufik Y. Progressive contraction of the latent HIV reservoir around a core of less-differentiated CD4? memory T Cells. Nat Commun. Nov. 10, 2014;5:5407.
Johnson JA, Li JF, Wei X, Lipscomb J, Irlbeck D, Craig C, et al. Minority HIV-1 drug resistance mutations are present in antiretroviral treatment-naive populations and associate with reduced treatment efficacy. PLOS medicine. 2008;5(7):e158. Epub Aug. 1, 2008.
Juffermans, NP, Paxton WA, Dekkers PE, Verbon A, de Jonge E, Speelman P, van Deventer SJ, van der Poll T. Up-regulation of HIV coreceptors CXCR4 and CCR5 on CD4+ T cells during human endotoxemia and after stimulation with (myco)bacterial antigens: the role of cytokines. Blood, 2000; 96(8), 2649-2654.
Kapoor A, Jones M, Shafer RW, Rhee SY, Kazanjian P, Delwart EL. Sequencing-based detection of low-frequency human immunodeficiency virus type 1 drug-resistant mutants by an RNA/DNA heteroduplex generator-tracking assay. J Virol. Jul. 2004;78(13):7112-23.
Katsikis PD, Mueller YM, Villinger F. The cytokine network of acute HIV infection: a promising target for vaccines and therapy to reduce viral set-point? PLOS Pathog. Aug. 2011;7(8):e1002055. doi: 10.1371/journal.ppat.1002055. Epub Aug. 11, 2011.
Kottilil S, Chun TW, Moir S, Liu S, Mclaughlin M, Hallahan CW, Maldarelli F, Corey L, Fauci AS. Innate immunity in human immunodeficiency virus infection: effect of viremia on natural killer cell function. J Infect Dis. Apr. 1, 2003;187(7):1038-45. Epub Mar. 13, 2003.
Kourteva Y, De Pasquale M, Allos T, McMunn C, D'Aquila RT. APOBEC3G expression and hypermutation are inversely associated with human immunodeficiency virus type 1 (HIV-1) burden in vivo. Virology. 2012;430(1):1-9. Epub May 15, 2012.
Laird GM, Bullen CK, Rosenbloom DI, Martin AR, Hill AL, Durand CM, Siliciano JD, Siliciano RF. Ex vivo analysis identifies effective HIV-1 latency-reversing drug combinations. J Clin Invest. May 2015;125(5):1901-12.
Lewin SR. Evans VA Elliott JH Spire B. Chomont N. Finding a cure for HIV: will it ever be achievable? Journal of the International AIDS Society. 2011;14:4. Epub Jan. 25, 2011.
Lewin SR, Rouzioux C. HIV cure and eradication: how will we get from the laboratory to effective clinical trials? Aids. 2011;25(7):885-97. Epub Mar. 23, 2011.
Li Q, Smith AJ, Schacker TW, Carlis JV, Duan L, Reilly CS, Haase AT. Microarray analysis of lymphatic tissue reveals stage-specific, gene expression signatures in HIV-1 infection. J Immunol. Aug. 1, 2009;183(3):1975-82. doi: 10.4049/immunol.0803222. Epub Jul. 13, 2009.
Li Y, Kurlander RJ. Comparison of anti-CD3 and anti-CD28-coated beads with soluble anti-CD3 for expanding human T cells: differing impact on CD8 T cell phenotype and responsiveness to restimulation. Journal of translational medicine. 2010;8:104. Epub Oct. 28, 2010.
Lim et al., Clinical and Diagnostic Laboratory Immunology, 1998, 5(3):392-398.
Liu L, May S, Richman DD, Hecht FM, Markowitz M, Daar ES, et al. Comparison of algorithms that interpret genotypic HIV-1 drug resistance to determine the prevalence of transmitted drug resistance. Aids. 2008;22(7):835-9. Epub Apr. 23, 2008.
Luo K, Wang T, Liu B, Tian C, Xiao Z, Kappes J, et al. Cytidine deaminases APOBEC3G and APOBEC3F interact with human immunodeficiency virus type 1 integrase and inhibit proviral DNA formation. J Virol. 2007;81(13):7238-48. Epub Apr. 13, 2007.
MacPherson JI, Dickerson JE, Pinney JW, Robertson DL Patterns of HIV-1 protein interaction identify perturbed host-cellular subsystems. PLoS Comput Biol. Jul. 29, 2010;6(7):e1000863.
Maldarelli F, Wu X, Su L, Simonetti FR, Shao W, Hill S, Spindler J, Ferris AL, Mellors JW, Kearney MF, Coffin JM, Hughes SH. Specific HIV integration sites are linked to clonal expansion and persistence of infected cells. Science. 2014;345(6193):179-183.
Mallal S, Phillips E, Carosi G, Molina JM, Workman C, Tomazic J, et al. HLA-B*5701 screening for hypersensitivity to abacavir. The New England journal of medicine. 2008;358(6):568-79. Epub Feb. 8, 2008.
Marcello A. Latency: the hidden HIV-1 challenge. Retrovirology. 2006;3:7. Epub Jan. 18, 2006.

\* cited by examiner

UTILITIES OF STIMULATED WHOLE BLOOD CULTURE SYSTEMS

CROSS-REFERENCE TO RELATED APPLICATION

This application is a Division of U.S. application Ser. No. 14/208,086 which issued on Feb. 4, 2020 as U.S. Pat. No. 10,550,419 and claims priority to provisional application Ser. No. 61/780,663 filed Mar. 13, 2013, each of which are incorporated by reference herein in their entireties.

BACKGROUND OF THE INVENTION

This invention pertains to uses of stimulated whole blood collection devices and their utilities related to virologic infections, viral vector systems and viral treatment regimens, including latent cellular reservoirs and drug resistance.

Despite successes of highly active antiretroviral therapy (HAART) inhibiting Human Immunodeficiency Virus (HIV) replication, viral latency and low-level replication enable viral persistence and prevent eradication. Achievement of either long-term HIV control in the absence of ART (functional cure) or complete elimination of HIV from the human body (sterilizing cure) remain unmet challenges (2, 3). Although a variety of cell types such as macrophages and long-lived resting memory $CD4^+$ T cells are known viral reservoirs (7, 15), these and other latent HIV reservoirs are difficult to investigate owing to sampling volumes and limited availability of ex vivo human tissues. Understanding molecular mechanisms of HIV-1 latency in vivo and the dynamics of the latent reservoir is also complicated by the small numbers of latently infected cells and the lack of known phenotypic markers distinguishing them from uninfected ones.

Recently, the size of the latently infected virus reservoir in resting memory $CD4^+$ T cells has been determined to be 60-fold greater than previously estimated [Y-C Ho 2013]. Current methods of T-cell activation reverse less than 1% of provirus to release infectious virus. Methods and therapeutic treatments to clear provirus are urgently needed to provide either functional or sterilizing curative strategies. The present invention provides a method for testing such strategies using whole blood culture to measure virus production, provirus, activation and inhibition of virus production.

Current knowledge of the latent viral state is largely based upon limited animal models (4, 5, 11, 16) and multiple T cell models (17) that can be implemented in laboratory settings. Such models allow investigators to manipulate conditions and clinical parameters otherwise difficult to control for in humans. Leukophoresis; sucrose or ficoll gradients; and antibody affinity/magnetic beads techniques are currently employed for the isolation of primary white blood cells from donors. Such processes may disturb the natural state of recovered cells and remove (or add) critical factors altering their normal function. While useful, none of these experimental systems sufficiently replicates biological properties of HIV infection, residing in multiple cell types and established through complex mechanisms. Therefore, to support goals of discovering and developing methods to purge the latent reservoir, and for identifying useful therapeutic patient strategies there is a critical need for improved models useful for determining the source and dynamics of persistent virus, for conducting sampling of specimens from naturally infected individuals, for characterizing activation of latent reservoirs and for identifying useful markers corresponding to latently infected T cells. Incremental changes in reservoir size and activity need to be consistently detected in order to identify promising therapies in a cost-effective and safe manner, reducing exposures to individuals. Novel and improved assays are also required to provide reproducible, sensitive, precise, feasible, accessible and standardizable measurements of persistent replication-competent virus, HIV DNA genomes, and tissue reservoirs of HIV in support of large clinical trials, for research purposes and for personalized medicine. Stimulated whole blood culture provides commercially available products to noninvasively evaluate the

- extent of viral replication
- cellular sources of virus production
- insult to the immune system
- extant viral quasispecies
- activation process of latently infected cellular reservoirs
- effectiveness of new curative strategies
- personalized approaches for patient treatment
- effects of virus, bacteria or fungal coinfections
- cotherapeutic complications Drug Resistance Current estimates report 34.0 million people are living with HIV globally; 2.5 million people were newly infected in 2011 (1). In the United States, 1.1 million people are estimated to be living with HIV; approximately 50,000 people are newly infected each year. Approximately 18% of U.S. HIV-infected individuals are unaware of their infection status; some evidence indicates that ~half of new infections occur between 15-24 years of age (2).

Although antiretroviral therapeutics (ARTs) have greatly extended lifespans, new challenges related to long-term management of HIV have arisen. Daily adherence (>95%) to multiple therapeutics is mandatory to control disease progression (3, 4). FDA-approved ART drugs belong to limited drug classes. HIV produces very large numbers of mutational variants owing to high rates of virus particle production ($10^9$-$10^{10}$ per day, unsuppressed), careless genomic proof-reading (reverse transcriptase) and selective drug pressure (5). Despite years of continuous successful ART suppression, viral reservoirs lurking in cells and physiological compartments threaten to reestablish active infection (6), typically within ~9 to days upon ART withdrawal or treatment interruption (7). Resurgence of virus reflects an archived historical collection of lifelong mutational variants, including their ART resistance profiles (6, 8-11). As HIV-infected individuals are infected young and living longer, ART options for retaining antiviral activity dwindle. As such, ART resistance testing has become a standard of care in HIV infection management.

HIV is now largely considered a chronic disease. Consequently, drug resistance in the face of limited drug classes is a mounting problem (12) leading to treatment failure with virus production surges and associated health risks. Furthermore, in the U.S. it is reported that approximately 6-16% of newly diagnosed HIV-infected individuals are now initially resistant to at least one ART class of drugs at first line therapy due to transmitted drug resistant mutations, consequently increasing risks for treatment failure (13-19). The extent of drug resistance further correlates with duration of uncontrolled virological replication (20), and clinically presents as increasing plasma virus production (viremia), decreasing CD4+ T-cell counts and the onset of both AIDS and non-AIDS related conditions (21, 22). Poor control of HIV is associated with higher costs (23, 24). The goal of ART is to preserve T-cell counts (>350 counts/uL) and activity through control of viremia (<50 viral RNA copies/ mL) (25). There is currently no consensus on best treatment strategies for third-line treatment failure ("salvage therapy"); management of these patients is thus extremely challenging (26-29).

Since maintaining low to undetectable viremia (<50 copies/mL) with ART is the key to surviving HIV, detecting and quantifying drug resistance is critical for therapeutic selections (30, 31). The US Department of Health and Human Services (DHHS) guidelines for ART (25) state:

'Selection of a regimen should be individualized on the basis of virologic efficacy, toxicity, pill burden, dosing frequency, drug-drug interaction potential, resistance testing results, and comorbid conditions, and that based on individual patient characteristics and needs, in some instances, an alternative regimen may actually be a preferred regimen for a patient.'

Currently available FDA-approved resistance testing includes two genetic sequencing (genotyping) methods for detecting HIV genomic mutations. Alternative unapproved in vitro drug response (phenotyping) systems and other genotyping systems are also available to meet recommendations by the DHHS. Unfortunately, due to a lack of overall sensitivity, existing systems fail to adequately characterize viral load and mutational variants in that they require samples expressing HIV plasma viremia levels >500-1000 RNA copies/mL. Furthermore, the complexity of these detection platforms often necessitates the construction of analysis clones, recombinant vector systems, amplification of isolates or sequence-specific probes (32, 33). Current generation tools are lacking in overall sensitivity and specificity leading to as many much as 10-25% of minority virus quasispecies being overlooked. Test results also often require several weeks and rely upon complex assays performed by highly skilled staff using expensive instruments. Their utilization of historical data coupled with proprietary algorithms for interpretation sometimes lead to agreement failures (34-36). Furthermore, FDA-approved (2002-2003) genotyping is limited to (N)NRTI (non/nucleoside reverse transcriptase inhibitors) and PI (protease inhibitors) drug classes of HIV-1 subtype B, with integrase inhibitor resistance testing performed separately. For complex patterns of resistance, genotyping sequence comparisons cannot adequately predict responses (35, 37), for which time-consuming phenotyping assays are more appropriate. Expanding drug classes, emerging patterns of resistance and evolving virus strains (including non-B subtypes) argue for technological adaptation. The described invention addresses these shortcomings using a combination phenotyping/genotyping whole blood culture system that can directly amplify virus production from HIV-infected blood, directly test antiviral strategies and provide for analyses of virus mutations. The technology combines genotyping, phenotyping, viral tropism and host genetic HLA-B*5701 testing into one platform that can be performed in less than one week. It addresses prospects of a functional or sterilizing cure (55, 56) and pharmaceutical testing of new antiretroviral therapeutic candidates (57).

The invention combines genotyping and phenotyping through stimulated whole blood culture of HIV-infected donor blood. The standardizable incubation tubes require small volumes (1 mL/tube) of fresh blood to be collected into prefilled, sealed collection tubes containing supportive media, an anticoagulant, stimulants and/or inhibitors (38). Typically, there will be interrelated matched sets of 6-12 tubes per donor. T-cell expansion of HIV-infected cells using, for example, anti-CD3/anti-CD28, PHA (phytohemagglutinin) or viral proteins (39, 40) results in significant amplifications of virus particle production within 2-3 days (41). After gentle centrifugation of incubated samples, viral RNA (or proteins) can be quantified from collected supernatants using standard methods.

Flow cytometric analyses of cells obtained directly from whole blood cultures can be processed to define cellular factors including viral tropism (CXCR4 vs. CCR5) and HLA-B*5701 major histocompatibility complex expression. Blood collections from HIV-infected donors may range between 1.5 to $4.5\times10^6$ lymphocytes/tube ($3-8\times10^6$ total white blood cells/tube) easily providing $~10^6$ cells needed in replicate aliquots. Following antibody labeling, red blood cells can be lysed and cells can be washed and fixed in paraformaldehyde. Cells can be analyzed by gating on lymphocytes (CD3/CD4/CD8/CD45, e.g.) and monocytes (CD14/CD16/HLA-DR/CD45, e.g.) together with forward and side scatter channels, or by other methods such as microscopy. The system is amenable to stimulations under matched stimulant/drug-treated conditions. This strategy addresses evolving drug-selective mutational resistances of HIV, expanding therapeutic developments, host-specific cellular responses, and potential contraindications of therapeutic interactions.

Isolating viral quasispecies directly from stimulated whole blood cultures as opposed to constructing plasmids or vectors confers significant and distinct staging advantages over existing technologies (42). Over the 2-3 day incubation period, stimulated T-cell expansion will directly amplify virus populations from their primary cellular sources. Activated, infected CD4 T-cells survive approximately 2.2 days and can produce between $10^3$ to $10^4$ virions over their lifespan (43, 44). Since the HIV generation time from infectivity to production is ~2.6 days, and the average viral decay half-life is ~2.1 days (43), the proposed technology directly amplifies virus production ex vivo rather than requiring an individual to risk periods of unsuppressed viremia required for other methods. Importantly, all causes of clinical mortality—both AIDS and non-AIDS—can be associated with the cumulative measure of virus burden (22) and should be avoided. In this way, stimulated virus production may be possible for individuals whose viremia is below 500 viral RNA copies/mL.

Secondly, comparative analyses using selected drugs or drug combinations can be tested in the context of individualized patient characteristics and needs. Drug resistance is not an all-or-nothing phenomenon in HIV management. Rather, therapeutic value may be assessed with dose adjustments or in combination with other ARTs. Currently available ART resistance genotyping assays cannot evaluate evolving drugs and therapies (40) targeting host receptors, inhibiting TAT-TAR interactions, acting upon transcription pathways or stimulating the latent reservoirs. While phenotyping assays evaluate drug responsiveness, these are performed with truncated virus populations using cell lines in time-consuming assays (33).

Thirdly, the technology allows for direct collection and analysis of virus-producing cells to determine viral tropism and host factors such as Human Leukocyte Antigen (HLA)-B*5701. Given the inspiring aviremic outcomes of a delta32 CCR5 mutation bone marrow transplant in the case of the "Berlin Patient" (45), focus on CCR5 receptor inhibitors has soared. Nonetheless, available resistance tests have been inadequate since no consistent pattern of resistance-associated variants has been identified in the highly variable HIV V3 loop (46, 47). Current methods for tropism testing (48) report maximum % inhibition (Phenosense®) or coreceptor selection (Trofile®). Testing for dual tropism (viruses using both CXCR4 and CCR5 coreceptors) is not currently available. By blocking the coreceptor with antibodies under stimulation, relative virus production (stimulated vs. stimulated+anti-CCR5 or anti-CXCR4) can be compared to determine activities for antiretroviral therapeutics such as Vicriviroc or Maraviroc.

Hypersensitivity reactions to Abacavir (NRTI) are largely (but not completely) associated with the HLA-B*5701 allele, requiring a screening test (usually phenotyping) prior to initiation of ART (49). Approximately 5-8% of the population carry this allele (50).

Finally, the system is amenable to developing possibilities for single cell detection systems, analysis of drug-drug interactions (other than ARTs), impacts of coinfections, contributions of relative and distinct cell populations and assessing efficacies of new virus eradication strategies. Isolation of virions, primary blood cells and soluble factors can each provide patient-specific information useful for clinical management of HIV infection and comorbid conditions.

DETAILED DESCRIPTION OF THE INVENTION

As HIV research requires in vitro models preserving physiological cellular interactions and accessible immune system measurements with and without stimulation, an instant leukocyte culture system (ILCS) is designed to capture virus production and associated cellular activity while minimizing sample collection and manipulation variables presented by leukophoresis (10, 14). Stimulated whole blood collections can be collected from HIV(+) donors, prefilled with cellular stimulants and/or therapeutics, together with supporting media, so that donors experience neither exposures nor risks different from a standard blood draw. Useful virus stimulants include, for example, anti-CD3/CD28; the phorbol ester Prostratin; concanavalin A; phorbol 12-myristate 13-acetate (PMA); Phytohaemagglutinin (PHA); Vorinostat, Valproic Acid; histone deacetylase inhibitors such as suberoylanilide hydroxamic acid (SAHA); protein kinase C activators such as Bryostatin; disulfram; Interleukin-2; Interleukin-7 or viral proteins (such as gp120, nef or tat) [N M Archin 2014; C N Chan 2013; S Deeks 2012; S R Lewin 2011; A Marcello, 2006]. Matched tubes containing stimulant/no stimulant/drug/therapeutic combinations provide for comparative analyses of responses from supernatants (soluble factors), recovered buffy coats (receptors, activation states, and intracellular proteins, cell-associated RNA, genomic DNA, mRNA), isolated oligonucleotide measures (RNA copies/mL) or virus particle proteins. Standard methods of analyses include, for example: flow cytometry, mass spectrometry, gel electrophoresis, Western blotting, polymerase chain reaction (PCR), imaging and capillary electrophoresis. Multilevel facets of proviral and/or active virus replication using stimulated whole blood culture systems provide an improved model for research and therapeutic applications. Further, virus inoculum can be introduced into a stimulated whole blood culture system to create an acute virus infection culture or to test a vaccine. Alternatively, a virus vector could be introduced or propagated in stimulated whole blood culture systems.

The present invention is directed to methods for the recognition and/or characterization of cellular virus production or virus inhibition in a biological sample, the relevant use of virus stimulants, and a kit. As used herein, "cellular virus production or virus inhibition" refers to changes in the numbers and expression rates of virus particles, particularly with respect to activation of latently infected cells harboring provirus in an inactive state. The changes in virus production can be altered by biological and/or chemical means. The production patterns can encompass one change of state or several changes of state.

As used herein, the term "biological sample" refers to a subset of tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A "biological sample" further refers to a homogenate, lysate or extract prepared from an organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "biological sample" can also refer to cells or tissue analyzed in vivo, e.g., without removal from animal. Typically, a "biological sample" will contain cells from the animal, but the term can also refer to non-cellular biological material, such as non-cellular fractions of blood, saliva, or urine, which can be used to measure the virus-associated polynucleotide or polypeptides levels. A "biological sample" further refers to a medium, such as a nutrient broth or gel in which cells have been propagated, which contains cellular components, such as, for example, proteins or nucleic acid molecules.

The virus production capacity of infected blood cells is in some cases associated with dynamic changes of state. The invention provides an extracorporeal, e.g., ex vivo, method that permits recognition and/or characterization of these transformations of cellular states. This can be utilized in a particularly advantageous manner for assessing particular HIV-infected cells—particularly latently infected cells—and the ability of drugs or stimulants to alter the production of virus from these cells. As used herein, the term "efficacy" refers to the degree to which a desired effect is obtained, particularly in relation to treating an infection.

Patient-specific differences with regard to the virus production patterns of the blood cells can also be determined such that, in principle, sub-typing of infection state is feasible, e.g., classification in patient subgroups. The sub-typing process can have important consequences for curative and therapeutic approaches. For example, the method according to the invention can be followed by an appropriate individual therapy. Furthermore, the method according to the invention is suitable to monitor manifested and treated infections. Therefore the method according to the invention can be applied in combination with a defined therapeutic measure.

The methods described herein make it possible to determine the influence of a therapeutic measure on virus production and integrated or nonintegrated latent provirus. For example, it is possible to examine which medicinal products are capable of producing or altering an HIV-infection by virus production inhibition or activation.

It is also possible to examine the associated immunological behavior of the blood cells over a longer period. For this purpose blood cells from an HIV-infected donor or patient can be monitored for alterations in their immunological behavior towards a stimulus response. HIV infection alters the responsiveness of immunological cells. This makes it possible to establish the dynamic fluctuations in the activity patterns of the blood cells.

Generally speaking, when examining stimulated blood cells and/or the culture medium, all cellular changes of state can be referred to, e.g., chemical, biochemical and/or biological changes of state of the stimulated blood cells and/or of the blood cells are measured. The chemical changes can be, for example, physico-chemical changes in state. Changes can include, for example, the calcium influx into the blood cells, pH value changes, membrane potentials and/or phosphorylation levels.

In one embodiment, the present invention is directed to methods of detecting altered states of cells wherein the culture medium of the cells is examined to determine the substances secreted into the culture medium by stimulated blood cells. Examination of the secreted substances can take place during the stimulation process or after the stimulation process at intervals that can be readily determined by one of skill in the art. The concentrations of the substances secreted by the stimulated blood cells are determined by methods described herein and known in the art. Whether secreted or not, changes in the expression levels of genes can be monitored to determine the activation state of cells. Biochemical molecules, e.g., expression products, mRNA, polypeptides, etc., are detectable and allow for the determination of the activation state of stimulated cells.

As used herein, the term "nucleic acid" refers to deoxyribonucleotides or ribonucleotides and polymers thereof in either single- or double-stranded form. The term encompasses a nucleic acid containing known nucleotide analogs or modified backbone residues or linkages, which are synthetic, naturally occurring, and non-naturally occurring, which have similar binding properties as the reference nucleic acids, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). A nucleic acid sequence also encompasses naturally-occurring allelic variants of said nucleic acid.

As used herein, the term "oligonucleotide" refers to a nucleic acid molecule consisting of two or more deoxyribonucleotides or ribonucleotides joined by phosphodiester bonds, and preferably containing between about 6 and about 300 nucleotides in length. The size of the oligonucleotide will depend on many factors, including the ultimate function or use of the oligonucleotide. Preferably, an oligonucleotide that functions, for example, as an extension primer will be sufficiently long to prime the synthesis of extension products in the presence of a catalyst, e.g., DNA polymerase, and deoxynucleotide triphosphates. As used herein, the term "oligonucleotide" further refers to an oligonucleotide that has been modified structurally ("modified oligonucleotide") but functions similarly to the unmodified oligonucleotide. A modified oligonucleotide can contain non-naturally occurring portions, such as altered sugar moieties or inter-sugar linkages, such as a phosphorothioate.

As used herein, the term "polypeptide" refers to a polymer in which the monomers are amino acids and are joined together through peptide or disulfide bonds. It also refers to either a full-length naturally-occurring amino acid sequence or a fragment thereof between about 8 and about 500 amino acids in length. Additionally, unnatural amino acids, for example, beta-alanine, phenyl-glycine and homoarginine can be included. All of the amino acids used in the present invention can be either the D- or L-optical isomer. A polypeptide sequence also encompasses naturally-occurring allelic variants of said polypeptide.

As used herein, the term "a significant change in the expression level" refers to either an increase or a decrease of the expression level from the control level by an amount greater than the standard error of the assay employed to assess expression. The term also refers to a change by preferably at least about 10%, about 20%, about 25%, about 30%, preferably at least about 40%, about 50%, more preferably at least about 60%, about 70%, or about 90%, about 100%, about 150%, or about 200%, or greater. As used herein, the term "gene" refers to a nucleic acid sequence that encodes and regulates expression of a polypeptide. A gene includes, therefore, regulatory elements, e.g., promoters, splice sites, enhancers, repressor binding sites, etc. A gene can have many different "alleles," which are sequence variations that can affect the polypeptide sequence or expression level, or have no effect on the polypeptide. A gene can include one or more "open reading frames", which are nucleic acid sequences that encode a contiguous polypeptide. A gene can be present either endogenously or exogenously.

The present invention also relates to methods for determining genes that are differentially expressed, e.g., create cellular activity patterns, in response to different stimuli. The particular genes, herein referred to as "informative genes", are identified in cells, e.g., blood cells that have been exposed to a particular stimulus or have been induced to produce virus. Differential expression of informative genes can relate to, for example, differences in expression relative to an unstimulated state, or differences in expression observed over a range of two or more different stimulatory factors. A subset or all informative genes can be assayed for gene expression to generate an "expression profile" that includes genes that are characteristic of a particular cellular activity pattern. As used herein, an "expression profile" refers to the level or amount of gene expression of one or more informative genes in a given sample of cells at one or more time points. A "reference" expression profile is a profile of a particular set of informative genes under particular conditions such that the expression profile is characteristic of a particular condition. For example, a reference expression profile that quantitatively describes the expression of the informative genes listed in the Tables can be used as a reference expression profile. Thus by comparing gene expression from a cell or tissue samples with a reference expression profiles is indicative of a particular cellular activity pattern.

As used herein, the term "expression level" refers to the amount of virus production or mRNA transcribed from its corresponding gene, or other gene product, that is present in a biological sample. The expression level can be detected with or without comparison to a level from a control sample or a level expected of a control sample. A "control level" refers to a standard level of a biomarker by which a change is measured against. In one embodiment, the "control level" can be a normal level of a biomarker nucleic acid expression, or a biomarker polypeptide, or a biomarker biological activity from normal or healthy cells, tissues, or subjects, or from a population of normal or healthy cells, tissues, or subjects. The term "control expression level" can also refer to an established level of virus production that has been previously established based on measurement from HIV-infected subjects.

As used herein, "detecting" refers to the identification of the presence or absence of a molecule in a sample. Where the molecule to be detected is a polypeptide, the step of detecting can be performed, for example, by binding the polypeptide to an antibody that is detectably labeled. A detectable label is a molecule that is capable of generating, either independently, or in response to a stimulus, an observable signal. A detectable label can be, but is not limited to a fluorescent label, a chromogenic label, a luminescent label, or a radioactive label. Methods for "detecting" a label include, for example, quantitative and qualitative methods adapted for standard or confocal microscopy, flow-cytometry analysis, and those adapted for high throughput methods involving multiwell plates, arrays, microarrays and microbead multiplexing. One of ordinary skill in the art can select appropriate filter sets and excitation energy sources for the detection of fluorescent emission from a given fluorescent polypeptide or dye. "Detecting" as used herein can also include the use of multiple antibodies to a polypeptide to be detected, wherein the multiple antibodies bind to different epitopes on the polypeptide to be detected. Antibodies used in this manner can employ two or more detectable labels, and can include, for example a FRET (fluorescence resonance energy transfer) pair. A polypeptide molecule is "detected" according to the present invention when the level of detectable signal is at all greater than the background level of the detectable label, or where the level of measured polypeptide is at all greater than the level measured in a control sample.

As used herein, "detecting" also refers to identification of the presence of a target nucleic acid molecule, for example, by a process wherein the signal generated by a directly or indirectly labeled probe nucleic acid molecule is measured or observed. Detection of the nucleic acid is directly indicative of the presence, and thus the detection, of a target nucleic acid, such as a sequence encoding a marker gene, a virus particle, an integrated provirus or an unintegrated provirus. Methods and techniques for "detecting" fluorescent, radioactive, and other chemical labels may be found in Ausubel et al. (1995, Short Protocols in Molecular Biology, 3rd Ed. John Wiley and Sons, Inc.).

Alternatively, a nucleic acid can be "indirectly detected" wherein a moiety is attached to a probe nucleic acid that will hybridize with the target, wherein the moiety comprises, for example, an enzyme activity, allowing detection of the target in the presence of an appropriate substrate, or a specific antigen or other marker allowing detection by addition of an antibody or other specific indicator. Alternatively, a target nucleic acid molecule can be detected by amplifying a nucleic acid sample prepared from a patient clinical sample, using oligonucleotide primers that are specifically designed to hybridize with a portion of the target nucleic acid sequence. Quantitative amplification methods, such as, but not limited to TaqMan, Abbott or Siemens (commercially available quantitative PCR systems) can also be used to "detect" a target nucleic acid according to the invention. A nucleic acid molecule is "detected" as used herein where the level of nucleic acid measured (such as by quantitative PCR), or the level of detectable signal provided by the detectable label is above the background level.

Nucleic acid molecules can be detected and/or isolated by specific hybridization under particular stringency conditions. "Stringency conditions" for hybridization is a term of art that refers to incubation and wash conditions, e.g., conditions of temperature and buffer concentration, which permit hybridization of a particular nucleic acid to a second nucleic acid. The first nucleic acid can be perfectly complementary to the second, or the first and second can share some degree of complementarity less than perfect (e.g., 70%, 75%, 85%, 95%). For example, certain high stringency conditions can be used that distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in Current Protocols in Molecular Biology (Ausubel, F. M. et al., "Current Protocols in Molecular Biology", John Wiley & Sons, (1998), the entire teachings of which are incorporated by reference herein). The conditions that determine the stringency of hybridization depend on parameters such as, for example, ionic strength, temperature, the concentration of destabilizing agents such as formamide or denaturing agents such as SDS, and factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules.

The methods of the present invention are useful for diagnosing or characterizing HIV virus infections. Diagnosis can be the early detection of virus production during acute infection. The methods described herein are also useful for monitoring the progression of HIV virus infection or the efficacy of antiviral therapeutic regimens. This monitoring and characterizing of an HIV infection refers to, for example, the measurement of a change in virus production or provirus levels before and after treatment with a therapeutic compound. In this case, a change in virus production in response to a therapeutic compound refers to either an increase or a decrease by at least about 10% relative to untreated. Alternatively, in the amount of the marker provirus presented in a clinical sample, in response to the presence of a therapeutic compound relative to the expression level in the absence of the therapeutic compound.

As used herein, the term "antibody" refers to the conventional immunoglobulin molecule, as well as fragments thereof that are also specifically reactive with one of the subject polypeptides. Antibodies can be fragmented using conventional techniques and the fragments screened for utility in the same manner as described herein below for whole antibodies. For example, F(ab).sub.2 fragments can be generated by treating antibody with pepsin. The resulting F(ab).sub.2 fragments can be treated to reduce disulfide bridges to produce Fab fragments. The antibodies of the present invention are further intended to include bispecific, single-chain, and chimeric and humanized molecules having affinity for a polypeptide conferred by at least one CDR region of the antibody. In preferred embodiments, the antibodies further comprise a label attached thereto and able to be detected (e.g., the label can be a radioisotope, fluorescent compound, chemiluminescent compound, enzyme, or enzyme co-factor). A "monoclonal antibody" is an antibody that recognizes only one epitope of an antigen. This type of antibodies is produced, for example, by the daughter cells of a single antibody-producing hybridoma.

An antibody of the present invention can include, but is not limited to, polyclonal, monoclonal, multispecific, human, humanized, or chimeric antibodies, single chain antibodies, Fab fragments, Fv fragments, F(ab') fragments, fragments produced by a Fab expression library, anti-iodiotypic antibodies, or other epitope binding polypeptide. Preferably, an antibody, useful in the present invention for the detection of a polypeptide, is a human antibody or fragment thereof, including scFv, Fab, Fab', F(ab'), Fd, single chain antibody, of Fv. An antibody can include a complete heavy or light chain constant region, or a portion thereof, or an absence thereof. An antibody can be obtained from a host, such as rabbit, mouse, rat, donkey, sheep, goat, guinea pig, camel, horse, or chicken. In one embodiment, an antibody useful in the invention can be a humanized antibody, in which amino acids have been replaced in the non-antigen binding regions in order to more closely resemble a human antibody, while still retaining the original binding ability. Methods for making humanized antibodies are known in the art (Teng et al., Proc. Natl. Acad. Sci. USA, 80:7308-7312, 1983; Kozbor et al., Immunology Today, 4:7279, 1983; Olsson et al., Meth. Enzymol., 92:3-16, 1982; WO 92/06193; and EP 0239400).

A non-immunoglobulin binding scaffold can also be used to detect targets as provided by the present invention. Avimers (avidity multimers) or aptamers, for example, can be used to bind specific targets. Other non-immunoglobulin binding scaffolds can be used based on, for example, receptors, protein A, the lipocalins, a fibronectin domain, an ankyrin consensus repeat domain, and thioredoxin. These non-immunoglobulin binding scaffolds can be, for example, detectably labeled, thereby allowing for the detection of a specific binding target.

In addition to detecting secreted substances, activation markers of the cells can be examined at the transcriptional, translational and/or post-translational level, preferably accompanied by the determination of their concentrations. Methods for determining changes include, for example, an immunoassay or electrophoretic methods. The immunoassays are generally based on the recognition of a target molecule by specific antibodies. An appropriate immunoassay for example is the ELISA method (enzyme-linked immunosorbant assay). An appropriate electrophoretic method for determining the concentration is, for instance, gel electrophoresis, particularly the two-dimensional polyacrylamide gel electrophoresis (2D PAGE). Furthermore, array technologies and, in particular, multiplex bead arrays or planar arrays are also useful for determining changes in expression levels.

The substances secreted by the stimulated blood can be "messenger" substances, e.g., mediators. The secreted substances can be proteins and/or peptides. For example, the proteins can be receptors and/or proteins with enzymatic activity. The secreted substances can be glycosylated proteins and/or peptides, and the state of glycosylation can also be determined to indicate changes in the activation state of the cells. The substances secreted by the stimulated blood cells can be low-molecular messenger substances, in particular radical oxygen compounds, lipidic messenger substances, cytokines, chemokines, soluble receptors and/or adhesion molecules. The secreted substances can be membrane-enwrapped vesicles, particularly exosomes and/or nucleosomes.

In one embodiment of the invention, the stimulated blood cells are recovered from the culture medium for the purpose of examination. For example, the blood cells can be recovered by means of centrifugation techniques known to those of skill in the art, e.g., gradient centrifugation or other separation methods using antibodies or specific binding structures employed to positively or negatively select cell populations and subpopulations. The recovery of the blood cells can also be performed with magnetic or flow-cytometric sorting technology.

When the stimulated blood cells are examined, gene products formed by the blood cells can also be examined. For example, RNA that is formed by the blood cells, especially viral RNA, viral DNA and mRNA (messenger RNA), can be analyzed. RNA and DNA formed in cells can be isolated by methods known in the art and quantitated, for example, by hybridization assays, e.g., hybridization assays performed on chips containing microarrays. The RNA from the blood cells can be isolated, for example, by means of extraction. Isolated RNA can be subjected to amplification, in particular a polymerase chain reaction with reverse transcriptase (RT-PCR) or nested PCR. Additional methods for detecting and quantitating RNA expression include, for example, Northern blotting or FISH (fluorescence in situ hybridization).

In addition, when the blood cells are examined, expression levels of proteins and/or peptides and/or virus particles can be determined. It is therefore possible to create expression patterns or profiles for examining proteins and/or peptides correlating with virus production or responses to therapeutic interventions.

Apoptotic signal pathways and processes in the stimulated blood cells can be determined. It is primarily the expression of signal transducers and/or receptors on and/or in the blood cells that are examined. Special priority is given to determining the density of the signal transducers and/or receptors on and/or in the blood cells. In addition, it is possible to examine the induction of enzymatic activities. For example, but not limited to, the enzymatic activities of phospholipases, cyclooxygenases, protein kinases, PARP (polyADP Ribose Polymerase), matrix-metalloproteinases, NADPH oxidases, phosphatases, kinases, ubiquitinylating enzymes and/or caspases can be examined. Methods for examining cellular signal transducers and/or receptors include, for example, analyses of surface markers and/or of phosphorylated signal transducer molecules, especially phosphorylated proteins. Appropriate analyses are based on, for example, histological staining techniques or flow cytometric methods known in the art.

In another embodiment, modified cell nucleus constituents of blood cells are examined to determine the activation state of stimulated or infected blood cells. Modified cell nucleus constituents are, for example, DNA and formed microRNA. DNA modifications, e.g., methylation and/or acetylation, can also be determined to detect changes in the state of stimulated cells.

In one embodiment, immune cells, particularly immune cells of the peripheral blood, primarily leukocytes, are used as blood cells. The blood cells are preferably whole blood. Leukocytes that contain lymphocytes, dendritic cells and/or macrophages can in particular be used as suitable blood cells. Primarily the stimulated blood cells are leukocytes. The leukocytes are in particular granulocytes, lymphocytes, NK-cells, dendritic cells, monocytes as well as precursors of these kinds of differentiation stages. The blood cells can be present especially as PBMC (peripheral blood mononuclear cells), which are primarily obtained by means of density gradient centrifugation. Leukocytes acquired in this way include, for example, T lymphocytes, B lymphocytes, NK cells (natural killer cells), monocytes, dendritic cells, eosinophils, plasma cells, as well as precursors thereof.

The blood cells useful in the present invention can already be present in an activated state before they are stimulated. This means that the blood cells can be pre-activated by stimulants or infection state. The stimulants can be Toll-like receptor ligands. For example, the blood cells of a donor with HIV infection can be used.

The blood cells can be enriched from blood prior to the stimulation process. A sample of the whole blood can be transferred to the culture medium with the whole blood cells being stimulated at least by the TLR ligands. Generally speaking "whole blood" is taken to be blood with all its blood constituents, including the blood cells, the blood plasma and the biologically active factors contained therein, for example the coagulation factors and complement proteins. Whole blood can be fresh blood, preferably fresh patient blood. In particular, blood cells can be obtained from a donor at specific intervals over an extended period. These samples obtained at different time points can be examined with regard to their activity patterns to, for example, monitor the progression of HIV infection or to determine the efficacy of treating HIV infection. This enables the current immunological performance and virus-producing capacity of the blood cells to be observed over an extended period, if necessary.

In one embodiment, blood cells can be stimulated over a period between 0 and about 48 hours, in particular between about 2 and about 48 hours, between about 12 and about 36 hours, between about 10 and about 24 hours. In a preferred embodiment, cells can be stimulated over a period of about 24 hours. In other embodiment, blood cells are stimulated for about 1 to 30 min, in particular between about 1 and 10 min. This is especially advantageous for examining early signal transductions. In particular the method according to the invention can be implemented as an "ultra-quick test". In this way it is possible to capture and examine relatively unspecific indicators of cellular activity. For example the calcium influx into the blood cells, changes to the intracellular and extracellular pH value, the phosphorylation of proteins and/or the formation of cAMP/cGAMP can all be determined.

In another embodiment, blood cells are stimulated over a period of about 1 to about 4 hours (quick test). Such a test is useful to examine the secretion of substances, e.g., messenger substances. For example, it is possible to measure the release of interleukin 1 (IL-1), tumor necrosis factor .alpha. (TNF.alpha.), interleukin-8 (IL-8) granzyme B, tryptase, histamine and/or perforin, etc. The secreted substances are in particular substances that are already preformed in the blood cells. These are normally stored in the cells in secretory granules. In addition, within the stimulation time mentioned in this section, it is possible to examine the synthesis of low molecular substances, in particular of messenger substances, such as, for example, prostaglandins and leukotrienes, as well as, for example, to examine the redistribution of surface markers. It is further possible to examine cytotoxic responses to infected cells.

In another preferred form of implementation the blood cells are stimulated over a period of about 6 to about 24 hours. In this way it is possible to capture and examine specific indicators of cellular activity. Specific cellular activity indicators include, for example, cytokines, chemokines, surface receptors, enzymes and/or other proteins or peptides, chemicals (such as peroxides, nitrites, nitrates, singlet oxygen, etc.) and exosomes and/or nucleosomes. The surface receptors can be, for example, adhesion molecules.

In accordance with the invention the blood cells can be stimulated in hollow cylindrical vessels, particularly of the blood vial or syringe cylinder type. Vessels of this type are particularly suitable for stimulating the blood cells if during the stimulation process a supernatant and a sediment form; the latter must essentially consist of the blood cells. In particular, a syringe can have a plunger that can be broken off and a sealing cap that opens up the entire cross section of the syringe cylinder. Syringe cylinders of this type can be handled like test tubes or centrifuge tubes after the plunger has been broken off. After the stimulation period, particularly after a period of stimulation lasting for over about 6 hours, an optional valve plunger can be used to separate cells from supernatant. The supernatant flows through the valve plunger. After the pressing-in of the valve, the valve plunger closes of its own accord so that it is no longer possible for the blood cells to mix with the supernatant. This is particularly advantageous if the examination of the activity of the blood cells is performed in a different location than where they were stimulated. Furthermore, in many cases preference is given to freezing the sample to be examined if it is to be kept for an extended period. This causes the blood cells contained in the sample to burst open, thus releasing their intracellular substances. The inserted valve plunger prevents the substances thus released from distorting the measuring results.

The present invention also applies to the use of virus stimulants and inhibitors for diagnosing and/or treating HIV infections. HIV infection alters the normal functions of immunological cells. According to the invention the intention is for treatments to be associated with changes in virus production patterns.

In one embodiment, the stimulants and drugs used according to the invention are primarily present in a stable form that can be added prior to blood collection or frozen together with the supportive media.

In another embodiment, the present invention is directed to a kit for diagnosis and/or tracking the treatment of HIV that includes a vessel for stimulating or inhibiting virus production. Stimulants or drugs can be included in the kit. The vessel contains at least one stimulant or drug. The kit according to the invention can comprise, separately, a vessel and at least one stimulant or drug. In particular the vessel can be a blood test tube or a syringe cylinder. Furthermore, the kit can further comprise a culture medium for the blood cells. Moreover, the kit according to the invention can also comprise a set of instruments for taking blood samples.

From 1.0 mL of blood, between $3-9 \times 10^6$ white blood cells can typically be collected. Following incubation with a stimulant (between 5 and 72 hours, 37 degrees C.), supernatants can be collected by centrifugation, immediately tested or frozen and later analyzed for soluble factors. Corresponding buffy coats (white blood cells, WBC's) can be collected and analyzed using techniques such as flow cytometric analysis. Since lymphocytes typically range from 24-48% of total WBC's, between $1.3-4.7 \times 10^6$ lymphocytes can be collected, providing sufficient cell numbers to examine the CD4$^+$ memory cell reservoir by flow cytometry (250,000 typically needed). Cells can also be sorted into distinct populations (cell sorting) using characteristic protein surface or intracellular markers. Virus genomes, mRNA (messenger ribonucleic acids), viral proteins, virus particles and virus activity can also be measured from these culture systems, and further correlated with various factors to assess, for example, the state, cellular reservoirs, stimulus responses, or genetic variety of quasispecies. Cellular sources of virus production can be achieved using state of the art techniques such as FISH (fluorescence in situ hybridization) or flow virometry [A Arakelyan A, Fitzgerald W, Margolis L, Grivel J-C. Flow virometry: a nanoparticle based technology for analysis of individual viral particles. *J Clin Invest* 2013; 123:3716-3727].

Buffy coats from stimulated whole blood culture can be collected into centrifuge tubes; red cells can be lysed and cells can be labeled, for example, for CD4+, CD45RO, CCR7, HLA-DR, CD25, CD27, CD38, CD14 and CD16 to identify monocytes, monocyte/macrophages, naïve CD4+T cells, activated and resting CD4+ central memory and effector memory T cells (6, 12). Stimulation may reactivate latent virus in HAART-suppressed subjects; drugs or antibodies may inhibit such processes. Viral replication can be measured using, for example, commercially available real time PCR (polymerase chain reaction) techniques (such as Abbott, Siemens, Qiagen, e.g.); by intracellular mRNA probes (InCellDX, e.g.) (12); by p24 capsid ELISA (enzyme-linked immunosorbent assay) or multiplexing (Luminex, e.g); or by other methods. APOBEC3 can be measured in virus-producing cells by flow cytometry and in virions released in the supernatant [DePasquale, M PLoS One 2013]. Native immunity host factors, such as APOBEC3, can be identified and monitored in order to understand their role in HIV pathogenesis and how they can be exploited to reduce the viral burden (1, 9, 13). Proviral HIV load (both integrated and non-integrated) can be measured in unstimulated/stimulated primary blood mononuclear cells using techniques known in the art, such as nested PCR and Alu-qPCR (8).

The invention provides a method that permits the determination of the virological responses and activities in stimulated versus unstimulated whole blood cultures. Blood cells are stimulated in a culture medium (such as RPMI) and the stimulated blood cells, virus particles, cellular and viral genomic factors and/or culture medium can be examined or measured using methods known in the art. Potential therapeutic treatments can likewise be tested/added in this system for both potential risks and benefits. Such applications apply to a broad scale of therapeutic testing and development as well as to personalized therapeutic treatments of viral infections, especially suited to eradication and treatment strategies for HIV-1 infections.

In one embodiment, the present invention is directed to a method for monitoring virus production from HIV-infected cells comprising comparing the cellular virus production pattern of a biological sample from a subject to one or more control cellular virus production patterns, wherein a statistical difference of the sample to the control is indicative of antiviral or stimulatory responses. In one embodiment, the one or more control cellular virus production patterns are determined in blood cells stimulated with at least one drug or stimulant. In one embodiment, virus production is associated with a viremia (RNA copies/mL). In another embodiment, virus production is associated with integrated or nonintegrated provirus (virus DNA).

In another embodiment, the present invention is directed to a method for determining the efficacy of a drug or treatment for stimulating virus production from blood cells containing provirus. The method comprises comparing the cellular virus production pattern of a biological sample from an HIV-infected patient with one or more control cellular virus production activity patterns, wherein a statistical difference between one or more control cellular virus production activity patterns is indicative of the efficacy of the treatment for inhibiting or stimulating virus production.

In another embodiment, the present invention is directed to a kit comprising a vessel for stimulating blood cells comprising at least one virus-inducing stimulant.

In another embodiment, the present invention is directed to a method for the pre-clinical testing of an antiviral agent for a desired activity or lack of activity, comprising: a) using a cell culture system comprising mutually communicating first and second compartments, and further comprising a separation layer that is permeable to at least one substance secreted from a cell, wherein the first compartment comprises a syntopic tissue cell and immune cell culture, and wherein the second compartment comprises a blood cell culture; b) contacting the cell culture system with a candidate agent; c) incubating the cell culture system in the presence of the candidate agent; and d) analyzing virus production and/or cellular activity indicators, wherein the relative virus production is indicative of the presence or absence of a desired activity of the agent. In one embodiment, the cell culture system is primed with a mediator or activator prior to contact with the candidate agent. In one embodiment, the cells of the cell culture system are separated from the cell culture system prior to screening for cellular activity indicators.

EXAMPLE 1

Figure 1:
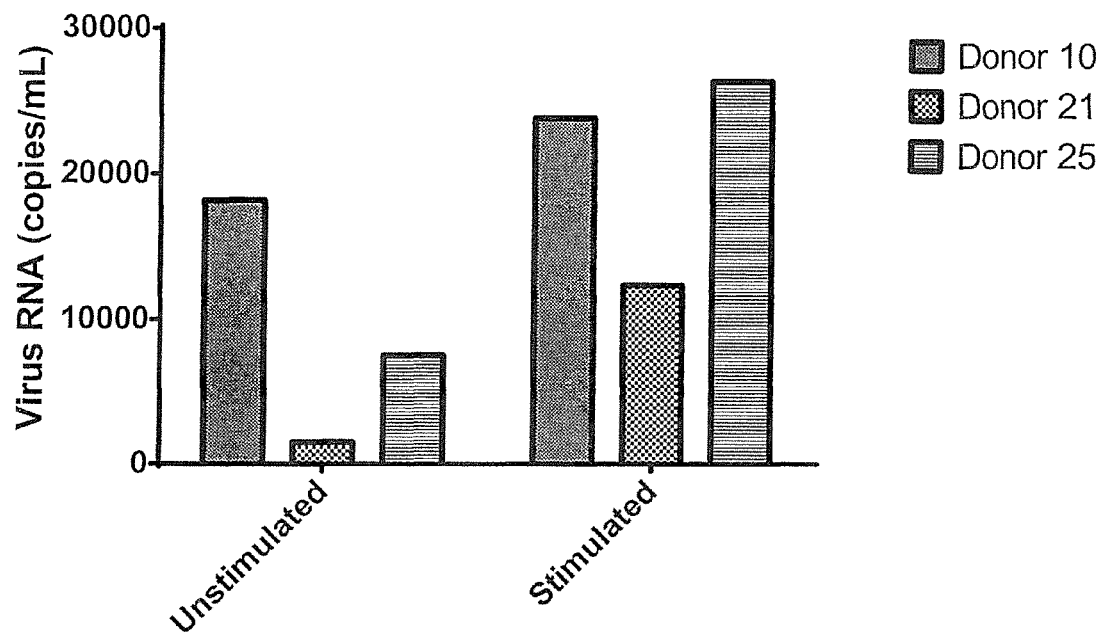
FIG. 1 depicts the amplification of virus production using stimulated whole blood cultures from HIV-infected blood.
Figure 2:
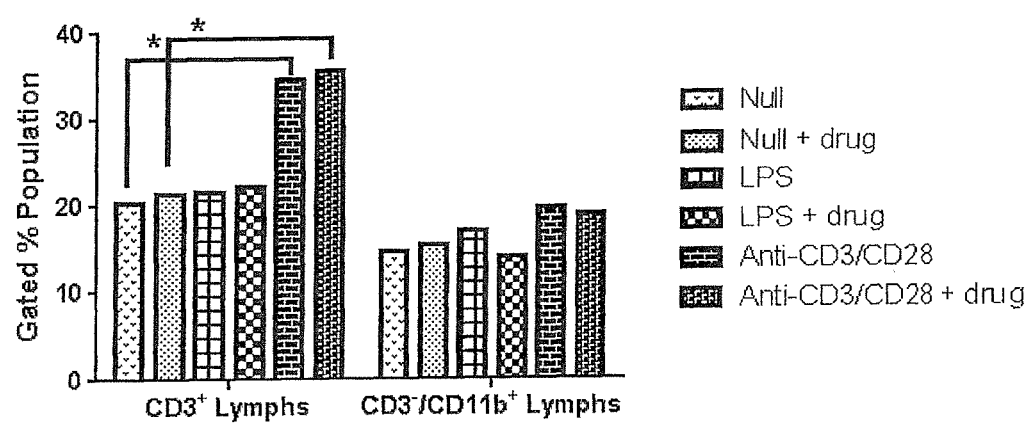
FIG. 2 illustrates effective stimulation and expansion of leukocytes using anti-CD3/anti-CD28 costimulation with HIV-infected donor blood, resulting in expansion of viral populations from their cell-specific origins within 48 hours at 37 degrees C.

Anti-CD3/Anti-CD28 Antibodies Increase Virus Production as Compared with Matched Unstimulated Cells Blood was collected into sequential preloaded (anticoagulant and stimulant in media) tubes and incubated 48 hours. Stimulants such as anti-CD3/anti-CD28 antibodies were matched to unstimulated tubes using whole blood culture at 37° C. in a tissue culture incubator with gases off. Samples were then centrifuged (140 g, 5 min) and supernatants were collected in duplicate vials (~0.8 mL each) and frozen (−80° C.). RNA was measured by RT-qPCR using the Abbott RealTime RNA assay. Recoveries were analyzed across matched donor sets (stimulated vs. unstimulated), reflecting relative virus amplification using the stimulant as shown in FIG. 1. Expansion of T-cell populations (identified by anti-CD3 antibodies) as illustrated in FIG. 2 are possible over this time period.

EXAMPLE 2

Figure 3:
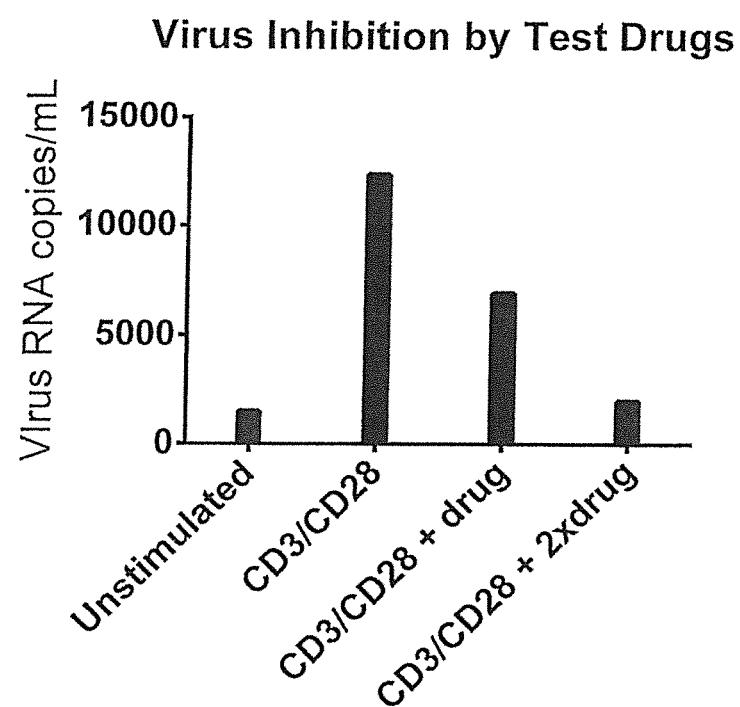
FIG. 3 illustrates virus production suppression of a candidate drug using stimulated whole blood cultures from HIV-infected blood.

Antiviral Drug Effects Evidenced by Reduced Virus Production in Stimulated Whole Blood Cultures Antiviral activities can be measured and compared using candidate therapeutics, drugs and/or stimulants. Blood was collected into sequential preloaded (anticoagulant and stimulant in media) tubes and incubated 48 hours. Anti-CD3/anti-CD28 antibodies stimulated virus production as compared with matched unstimulated tubes using whole blood culture at 37° C. in a tissue culture incubator with gases off. Samples were then centrifuged (140 g, 5 min) and supernatants were collected in duplicate vials (~0.8 mL each) and frozen (−80° C.). RNA was measured by RT-qPCR using the Abbott RealTime RNA assay. Relative virus inhibition correlates with increasing drug concentration as shown in FIG. 3.

EXAMPLE 3

Soluble Factor Responses Correlate with Virus Production Rates (Viremia)

Figure 4:
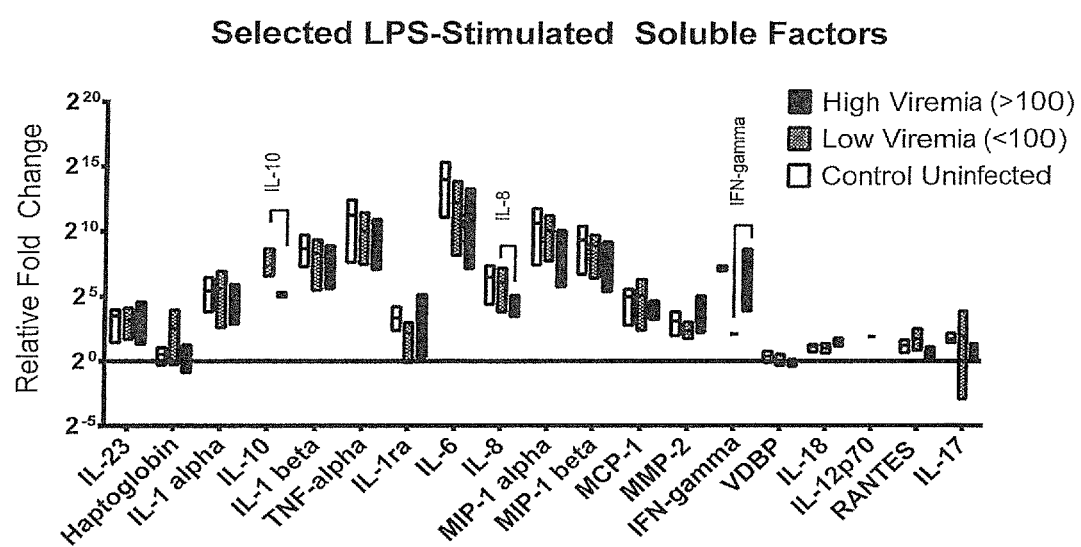
FIGS. 4-5 illustrates differences in stimulated immunological factors correlating with virus production rates (viremia) of HIV-infected whole blood cultures.
Figure 5:
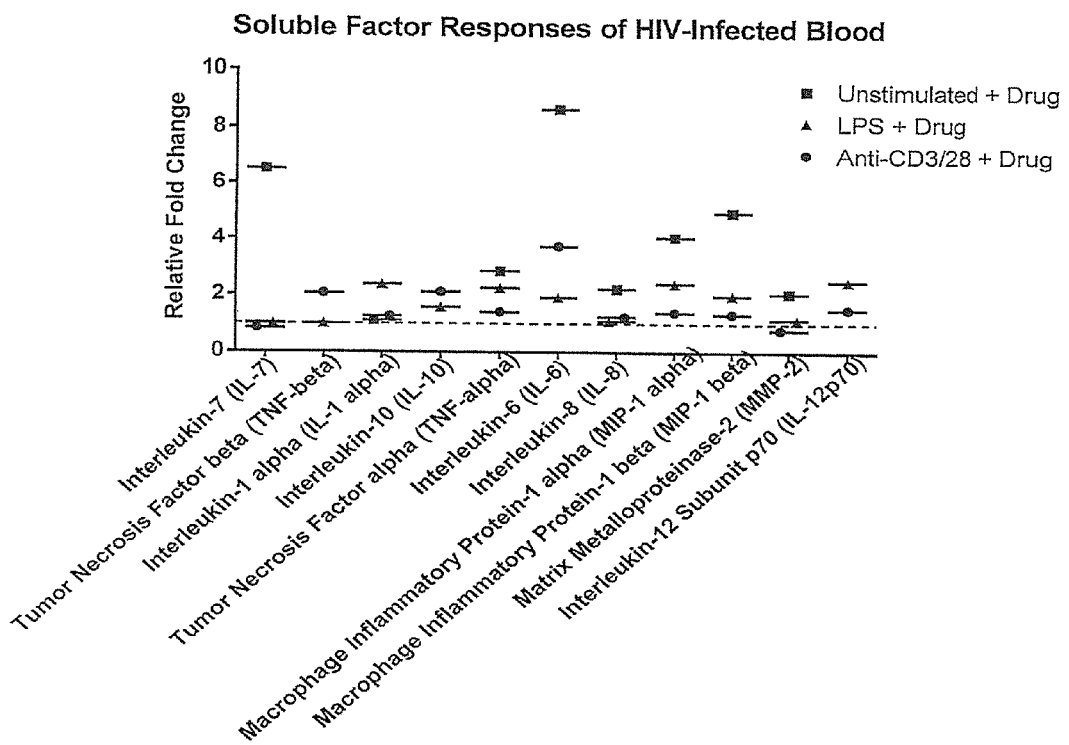
Figure 6:
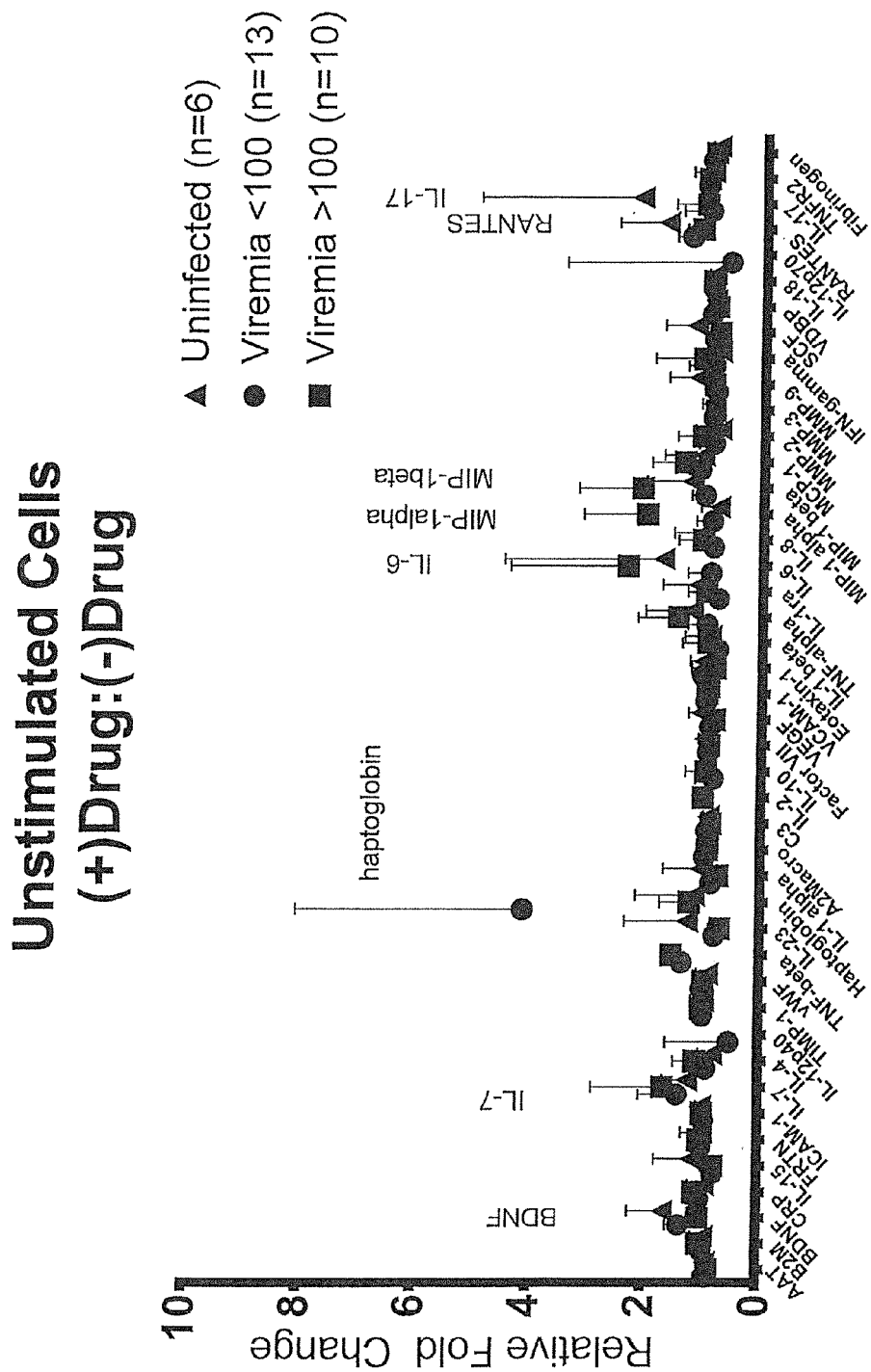
FIG. 6 illustrates differences in drug-treated immunological factors correlating with antiviral activities of HIV-infected whole blood cultures.

HIV-infected and uninfected blood was collected into sequential preloaded (anticoagulant and stimulant and/or drug in media) tubes and incubated 48 hours. Using lipopolysaccharide, differences in soluble factors from cellular responses correlate with virus production (viremia) for select factors. Whole blood was cultured at 37° C. in a tissue culture incubator with gases off. Samples were then centrifuged (140 g, 5 min) and supernatants were collected in duplicate vials (~0.8 mL each) and frozen (−80° C.). Supernatants were analyzed using Luminex fluorescently-labeled multiplex microbeads for 47 soluble factors. Correlations between viremia and immune cell stimulant responses (FIG. 4); immune cell stimulant responses with drug (FIG. 5); or drug-induced responses (FIG. 5) are illustrated.

REFERENCES

1. Chiu, Y. L., V. B. Soros, J. F. Kreisberg, K. Stopak, W. Yonemoto, and W. C. Greene. 2005. Cellular APOBEC3G restricts HIV-1 infection in resting CD4+ T cells. Nature 435:108-114.
2. Coiras, M., M. R. Lopez-Huertas, M. Perez-Olmeda, and J. Alcami. 2009. Understanding HIV-1 latency provides clues for the eradication of long-term reservoirs. Nat Rev Microbiol 7:798-812.
3. Colin, L., and C. Van Lint. 2009. Molecular control of HIV-1 postintegration latency: implications for the development of new therapeutic strategies. Retrovirology 6:111.
4. Deere, J. D., R. F. Schinazi, and T. W. North. 2011. Simian immunodeficiency virus macaque models of HIV latency. Curr Opin HIV AIDS 6:57-61.
5. Duyne, R. V., A. Narayanan, K. H. K, M. Saifuddin, L. Shultz, and F. Kashanchi. 2011. Humanized mouse models of HIV-1 latency. Curr HIV Res 9:595-605.
6. Fritsch, R. D., X. Shen, G. P. Sims, K. S. Hathcock, R. J. Hodes, and P. E. Lipsky. 2005. Stepwise differentiation of CD4 memory T cells defined by expression of CCR7 and CD27. J Immunol 175:6489-6497.
7. Haggerty, C. M., E. Pitt, and R. F. Siliciano. 2006. The latent reservoir for HIV-1 in resting CD4+T cells and other viral reservoirs during chronic infection: insights from treatment and treatment-interruption trials. Curr Opin HIV AIDS 1:62-68.
8. Kourteva, Y., M. De Pasquale, T. Alias, C. McMunn, and R. T. D'Aquila. 2012. APOBEC3G expression and hypermutation are inversely associated with human immunodeficiency virus type 1 (HIV-1) burden in vivo. Virology 430:1-9.
9. Luo, K., T. Wang, B. Liu, C. Tian, Z. Xiao, J. Kappes, and X. F. Yu. 2007. Cytidine deaminases APOBEC3G and APOBEC3F interact with human immunodeficiency virus type 1 integrase and inhibit proviral DNA formation. J Viral 81:7238-7248.
10. Nalos, M., S. Huang, R. Sluyter, A. Khan, B. Santner-Nanan, R. Nanan, and A. S. McLean. 2008. "Host tissue damage" signal ATP impairs IL-12 and IFNgamma secretion in LPS stimulated whole human blood. Intensive Care Med 34:1891-1897.
11. North, T. W., J. Higgins, J. D. Deere, T. L. Hayes, A. Villalobos, L. Adamson, B. L. Shacklett, R. F. Schinazi, and P. A. Luciw. 2010. Viral sanctuaries during highly active antiretroviral therapy in a nonhuman primate model for AIDS. J Virol 84:2913-2922.
12. Patterson, B. K., S. McCallister, M. Schutz, J. N. Siegel, K. Shults, Z. Flener, and A. Landay. 2001. Persistence of intracellular HIV-1 mRNA correlates with HIV-1-specific immune responses in infected subjects on stable HAART. Aids 15:1635-1641.
13. Romani, B., S. Engelbrecht, and R. H. Glashoff. 2009. Antiviral roles of APOBEC proteins against HIV-1 and suppression by Vif. Arch Virol 154:1579-1588.
14. Schmolz, M., T. L. Hurst, D. M. Bailey, J. R. Powell, R. J. Forsey, J. M. Thompson, C. Williams, and G. Pawelec. 2004. Validation of a new highly standardised, lab-independent whole-blood leukocyte function assay for clinical trials (ILCS). Exp Gerontol 39:667-671.
15. Smith, M. Z., F. Wightman, and S. R. Lewin. 2012. HIV reservoirs and strategies for eradication. Curr HIV/AIDS Rep 9:5-15.
16. Strickland, S. L., R. R. Gray, S. L. Lamers, T. H. Burdo, E. Huenink, D. J. Nolan, B. Nowlin, X. Alvarez, C. C. Midkiff, M. M. Goodenow, K. Williams, and M. Salemi. 2012. Efficient transmission and persistence of low-frequency SIVmac251 variants in CD8-depleted rhesus macaques with different neuropathology. J Gen Virol 93:925-938.
17. Tyagi, M., and F. Romerio. 2011. Models of HIV-1 persistence in the CD4+T cell compartment: past, present and future. Curr HIV Res 9:579-587.

What is claimed is:

1. A method for determining treatment of an HIV-infected subject, the method comprising:
   (a) obtaining whole blood from an HIV-infected subject, wherein the whole blood comprises latently-infected cells;
   (b) contacting the whole blood with a supportive medium and at least one virus stimulant and/or at least one virus inhibitor, thereby providing an admixture;
   (c) incubating the admixture for a period of time so as to induce virus production from the whole blood;
   (d) detecting in the incubated admixture the presence or absence of at least one of an HIV virus particle, an HIV viral nucleic acid, an HIV viral polypeptide, an HIV viral genomic sequence, infectivity, or a combination thereof,
   wherein the detecting further comprises comparing the presence or absence of at least one molecule in the admixture to the presence or absence of at least one molecule in a control sample, thereby identifying subject responsiveness to the stimulant and/or inhibitor, and
   (e) treating the subject with the at least one virus stimulant and/or at least one virus inhibitor.

2. The method of claim 1, wherein the presence or absence of at least one molecule in the admixture compared to the presence or absence of at least one molecule in a control sample is indicative of an alteration in provirus levels, virus production or virus inhibition.

3. The method according to claim 1, wherein the whole blood and the supportive medium and at least one virus stimulant and/or at least one virus inhibitor are admixed in a vessel.

4. The method of claim 3, wherein the vessel comprises a cylindrical vessel or multiwell plate.

5. The method according to claim 1, wherein the detecting comprises amplification of viral RNA, proviral DNA or viral DNA using polymerase chain reaction.

6. The method of claim 3, wherein the supportive medium and the virus stimulant and/or the virus inhibitor is present in the vessel prior to the admixing of the whole blood.

7. The method of claim 1, wherein the HIV virus stimulant comprises an antibody, a phorbol ester, a histone deacetylase inhibitor, a T-Cell Receptor (TCR) stimulant, a protein kinase C activator, a Toll Like Receptor (TLR) stimulant, a viral protein, a test therapeutic molecule, a cytokine, a chemokine, or a combination thereof.

8. The method of claim 1, further comprising separating the admixture into particular components, wherein separating comprises centrifugation, flow cytometry, extraction, affinity beads, a valve, antibody affinity, magnetic beads, mass spectrometry, or electrophoresis.

9. The method of claim 1, wherein detecting the presence or absence of a virus particle, a viral nucleic acid, a viral polypeptide, a viral genomic sequence, infectivity, or a combination thereof comprises incubating the admixture or component thereof with at least one antibody, at least one hybridization probe, at least one avimer, at least one aptamer or a combination thereof.

10. The method of claim 9, wherein the antibody, avimer, aptamer or hybridization probe is attached to a detectable label, wherein the detectable label comprises a fluorescent label, a chromogenic label, a luminescent label, a radioactive label, a magnetic label or a combination thereof.

11. The method of claim 1, wherein the admixture is incubated for a period up to 72 hours.

12. The method of claim 1, wherein the admixture is further incubated with at least one anticoagulant.

13. The method of claim 8, wherein at least one component comprises blood cells.

14. The method of claim 4, wherein the cylindrical vessel comprises a blood collection tube.

15. The method of claim 1, wherein the supportive medium comprises a cell or cellular component from a biological sample.

* * * * *